United States Patent
Butson et al.

(10) Patent No.: US 8,209,027 B2
(45) Date of Patent: *Jun. 26, 2012

(54) SYSTEM AND METHOD TO DESIGN STRUCTURE FOR DELIVERING ELECTRICAL ENERGY TO TISSUE

(75) Inventors: Christopher R. Butson, Cleveland Heights, OH (US); Cameron McIntyre, Cleveland, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 1453 days.

This patent is subject to a terminal disclaimer.

(21) Appl. No.: 11/606,260

(22) Filed: Nov. 28, 2006

(65) Prior Publication Data
US 2007/0083104 A1   Apr. 12, 2007

Related U.S. Application Data

(63) Continuation-in-part of application No. 10/885,982, filed on Jul. 7, 2004, now Pat. No. 7,346,382.

(60) Provisional application No. 60/740,031, filed on Nov. 28, 2005.

(51) Int. Cl.
*A61N 1/08* (2006.01)
*A61B 5/05* (2006.01)
(52) U.S. Cl. .......................... 607/59; 600/407
(58) Field of Classification Search ............. 607/115, 607/2, 116; 600/372, 587, 439, 427
See application file for complete search history.

(56) References Cited

U.S. PATENT DOCUMENTS

| | | | |
|---|---|---|---|
| 4,341,221 | A | 7/1982 | Testerman |
| 5,099,846 | A | 3/1992 | Hardy |
| 5,344,438 | A | 9/1994 | Testerman et al. |
| 5,361,763 | A | 11/1994 | Kao et al. |
| 5,452,407 | A | 9/1995 | Crook |
| 5,560,360 | A | 10/1996 | Filler et al. |
| 5,782,762 | A | 7/1998 | Vining |
| 5,938,688 | A | 8/1999 | Schiff |
| 6,066,163 | A | 5/2000 | John |
| 6,083,162 | A | 7/2000 | Vining |
| 6,106,460 | A | 8/2000 | Panescu et al. |
| 6,146,390 | A | 11/2000 | Heilbrun et al. |

(Continued)

FOREIGN PATENT DOCUMENTS
EP    1372780 A2    1/2004
(Continued)

OTHER PUBLICATIONS

Acar et al., "Safety Anterior Commissure-Posterior Commissure-Based Target Calculation of the Subthalamic Nucleus in Functional Stereotactic Procedures", *Stereotactic Funct. Neurosurg.*, 85:287-291, Aug. 2007.

(Continued)

*Primary Examiner* — Carl H. Layno
*Assistant Examiner* — Jon-Eric C. Morales
(74) *Attorney, Agent, or Firm* — Kenyon & Kenyon LLP

(57) ABSTRACT

A computer-assisted method can include defining a target volume of tissue activation to achieve a desired therapeutic effect for an identified anatomic region. At least one parameter can be computed for an electrode design as a function of the defined target volume of tissue activation. The computed at least one parameter can be stored in memory for the electrode design, which parameter can be utilized to construct an electrode.

11 Claims, 9 Drawing Sheets

U.S. PATENT DOCUMENTS

| | | |
|---|---|---|
| 6,240,308 B1 | 5/2001 | Hardy et al. |
| 6,289,239 B1 | 9/2001 | Panescu et al. |
| 6,301,492 B1 | 10/2001 | Zonenshayn |
| 6,310,619 B1 | 10/2001 | Rice |
| 6,343,226 B1 | 1/2002 | Sunde et al. |
| 6,351,675 B1 | 2/2002 | Tholen et al. |
| 6,389,311 B1 | 5/2002 | Whayne et al. |
| 6,421,566 B1 | 7/2002 | Holsheimer |
| 6,463,328 B1 | 10/2002 | John |
| 6,491,699 B1 | 12/2002 | Henderson et al. |
| 6,539,263 B1 | 3/2003 | Schiff et al. |
| 6,560,490 B2 | 5/2003 | Grill et al. |
| 6,622,048 B1 | 9/2003 | Mann et al. |
| 6,675,046 B2 | 1/2004 | Holsheimer |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,216,000 B2 | 5/2007 | Sieracki et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,252,090 B2 | 8/2007 | Goetz |
| 7,257,447 B2 | 8/2007 | Cates et al. |
| 7,266,412 B2 | 9/2007 | Stypulkowski |
| 7,324,851 B1 | 1/2008 | DiLorenzo |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 2002/0062143 A1 | 5/2002 | Baudino et al. |
| 2002/0123780 A1 | 9/2002 | Grill et al. |
| 2002/0128694 A1 | 9/2002 | Holsheimer |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0033380 A1 | 2/2005 | Tanner et al. |
| 2005/0070781 A1 | 3/2005 | Dawant et al. |
| 2005/0085714 A1 | 4/2005 | Foley et al. |
| 2005/0267347 A1 | 12/2005 | Oster |
| 2006/0020292 A1 | 1/2006 | Goetz et al. |
| 2006/0235472 A1 | 10/2006 | Goetz et al. |
| 2006/0259079 A1 | 11/2006 | King |
| 2007/0049817 A1 | 3/2007 | Preiss et al. |
| 2007/0123953 A1 | 5/2007 | Lee et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2008/0027514 A1 | 1/2008 | DeMulling et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0269588 A1 | 10/2008 | Csavoy et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0049280 A1 | 2/2010 | Goetz |
| 2011/0040351 A1* | 2/2011 | Butson et al. ............... 607/59 |

FOREIGN PATENT DOCUMENTS

| | | |
|---|---|---|
| WO | 02065896 A2 | 8/2002 |
| WO | 03086185 A1 | 10/2003 |

OTHER PUBLICATIONS

Andrade-Souza, "Comparison of Three Methods of Targeting the Subthalamic Nucleus for Chronic Stimulation in Parkinson's Disease", *Neurosurgery*, 56:360-368, Apr. 2005.

Anheim et al., "Improvement in Parkinson Disease by Subthalamic Nucleus Stimulation Based on Electrode Placement", *Arch Neurol.*, 65:612-616, May 2008.

Castro et al., "A Cross Validation Study of Deep Brain Stimulation Targeting: From Experts to Atlas-Based, Segmentation-Based and Automatic Registration Algorithms", *IEEE Transactions on Medical Imaging*, 25:1440-1450, Nov. 2006.

D'Haese et al., "Computer-Aided Placement of Deep Brain Stimulators: From Planning to Intraoperative Guidance", *IEEE Transaction on Medical Imaging*, 24:1469-1478, Nov. 2005.

Finnis et al., "Three-Dimensional Database of Subcortical Electrophysiology for Image-Guided Stereotactic Functional Neurosurgery", *IEEE Transactions on Medical Imaging*, 22:93-104, Jan. 2003.

Gross et al., "Electrophysiological Mapping for the Implantation of Deep Brain Stimulators for Parkinson's Disease and Tremor", *Movement Disorders*, 21:S259-S283, Jun. 2006.

Halpern et al., "Brain Shift During Deep Brain Stimulation Surgery for Parkinson's Disease", *Stereotact Funct. Neurosurg.*, 86:37-43, published online Sep. 2007.

Herzog et al., "Most Effective Stimulation Site in Subthalamic Deep Brain Stimulation for Parkinson's Disease", *Movement Disorders*, 19:1050-1099, published online Mar. 2004.

Jeon et al., A Feasibility Study of Optical Coherence Tomography for Guiding Deep Brain Probes, *Journal of Neuroscience Methods*, 154:96-101, Jun. 2006.

Khan et al., "Assessment of Brain Shift Related to Deep Brain Stimulation Surgery", *Sterreotact Funct. Neurosurg.*, 86:44-53, published online Sep. 2007.

Koop et al., "Improvement in a Quantitative Measure of Bradykinesia After Microelectrode Recording in Patients with Parkinson's Disease During Deep Brain Stimulation Surgery", *Movement Disorders*, 21:673-678, published online Jan. 2006.

Lemaire et al., "Brain Mapping in Stereotactic Surgery: A Brief Overview from the Probabilistic Targeting to the Patient-Based Anatomic Mapping", *NeuroImage*, 37:S109-S115, available online Jun. 2007.

Machado et al., "Deep Brain Stimulation for Parkinson's Disease: Surgical Technique and Perioperative Management", *Movement Disorders*, 21:S247-S258, Jun. 2006.

Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.

Miocinovic et al., "Cicerone: Stereotactic Neurophysiological Recording and Deep Brain Stimulation-Electrode Placement Software System", *Acta Neurochir Suppl.*, 97:561-567, Dec. 2007.

Moran et al., "Real-Time Refinment of Subthalamic Nucleous Targeting Using Bayesian Decision-Making on the Root Mean Square Measure", *Movement Disorders*, 21:1425-1431, published online Jun. 2006.

Saint-Cyr et al., "Localization of Clinically Effective Stimulating Electrodes in the Human Subthalamic Nucleus on Magnetic Resonance Imaging", *J. Neurosurg.*, 97:1152-1166, Nov. 2002.

Sakamoto et al., "Homogeneous Fluorescence Assays for RNA Diagnosis by Pyrene-Conjugated 2'-O-Methyloligoribonucleotides", *Nucleosides, Nucleotides, and Nucleric Acids*, 26:1659-1664, online publication Oct. 2007.

Starr et al., "Implantation of Deep Brain Stimulators into the Subthalamic Nucleus: Technical Approach and Magnetic Resonance Imaging-Verified Lead Locations", *J. Neurosurg.*, 97:370-387, Aug. 2002.

Sterio et al., "Neurophysiological Refinement of Subthalamic Nucleus Targeting", *Neurosurgery*, 50:58-69, Jan. 2002.

Winkler et al., The First Evaluation of Brain Shift During Functional Neurosurgery by Deformation Field Analysis, *J. Neurol. Neurosurg. Psychiatry*, 76:1161-1163, Aug. 2005.

Yelnik et al., "Localization of Stimulating Electrodes in Patients with Parkinson Disease by Using a Three-Dimensional Atlas-Magnetic Resonance Imaging Coregistration Method", *J. Neurosurg*, 99:89-99, Jul. 2003.

Yelnik et al., "A Three-Dimensional, Histological and Deformable Atlas of the Human Basal Ganglia. I. Atlas Construction Based on Immunohistochemical and MRI Data", *NeuroImage*, 34:618,-638,Jan. 2007.

Butson et al., Tissue and Electrode Capacitance Reduce Neural Activation Volumes During Deep Brain Stimulation, *Clinical Neurophysiology* 116 (2005) 2490-2500.

Butson et al., Sources and Effects of Electrode Impedance During Deep Brain Stimulation, *Clinical Neurophysiology*, 117 (2006) 447-454.

Butson et al., Role of Electrode Design on the Volume of Tissue Activated During Deep Brain Stimulation, *Journal of Neural Engineering*, 3 (2006) 1-8.

Butson et al., Patient-Specific Analysis of the Volume of Tissue Activated During Deep Brain Stimulation, *NeuroImage* (2006), doi:10.1016/j.neuroimage.2006.09/034.

Vitek, J. L., "Mechanisms of deep brain stimulation: excitation or inhibition", Mov. Disord., vol. 17 (Suppl. 3), (2002), S69-S72.

Voges, J., et al., "Bilateral high-frequency stimulation in the subthalamic nucleus for the treatment of Parkinson disease: correlation of therapeutic effect with anatomical electrode position", J. Neurosurg., 96(2), (Feb. 2002), 269-279.

Volkmann, J. et al "Intoducton to the pogramming of deep bain stmulators", Mov. Disord. vol. 17 (Suppl 3), (2002), S181-S187.

Wakana, S., et al., "Fiber tract-based atlas of human white matter anatomy", Radiology, 230(1), (Jan. 2004), 77-87.

Warman, E. N., et al, "Modeling the effects of electric felds on nerve fibers: Determinaton of excitation thresholds", IEEE Transactions on Biomedical Engineering, 39(12), (1992), 1244-1254.

Wu, Y. R., et al., "Does Stimulation of the GPi control dyskinesia by activating inhibitory axons?", Mov. Disord., vol. 16, (2001), 208-216.

Yelnik, J., et al., "Localization of stimulating electrodes in patients with Parkinson disease by using a three-dimensonal atlas-magnetic resonance imaging coregistration method", J Neuosurg., 99(1), (Jul. 2003), 89-99.

Yianni, John, et al., "Globus pallidus internus deep brain stimulation for dystonic conditions: a prospective audit", Mov. Disord., vol. 18, (2003), 436-442.

Zonenshayn, M., et al., "Comparison of anatomic and neurophysiological methods for subthalamic nucleus targeting", Neurosurgery, 47(2), (Aug. 2000), 282-294.

Miranda P et al. The Electric Field Induced in the Brain by Magnetic Stimulation: a 3-D Finite-Element Analysis of the Effect of TissueHeterogeneity and Anisotropy. IEEE Transactions on Biomedical Engineering. 50(9): p. 1074-1085. (Sep. 2003).

Miranda P et al. The distribution of currents inducedin the brain by Magnetic Stimulation: a finite element analysis incorporating DT-MRI-derived conductivity data. Proc. Intl. Soc. Mag. Reson. Med. vol. 9: p. 1540. (2001).

Da Silva et al., A primer on diffusion tensor imaging of anatomical substructures, Neurosurg Focus 15(1): p. 1-4, Article 4 (2003).

Dawant, B. M., et al., "Computerized atlas-guided positioning of deep brain stimulators: a feasibility study", Biomedical Image registration, Second International Workshop, WBIR 2003, Revised Papers (Lecture notes in Comput. Sci. vol. 2717,Springer-Verlag Berlin, Germany,(2003), 142-150.

Haiying, L., et al., "Intra-operative MR-guided DBS implantation for treating PD and ET", Proceedings of SPIE vol. 4319, Department of Radiology & Neurosurgery, University of Minnesota, Minneapolis, MN 55455, (2001), 272-276.

Mcientyre, C. C., et al., "Electric Field and Stimulationg Influence generated by Deep Brain Stimulation of the Subthalamaic Nucleus", Clinical Neurophyssiology vol. 115 (3), International Federation of Clinical Neurophysiology, published by elsevier Ireland Ltd., (Mar. 2004), 589-595.

Mcientyre, C C., et al., "Model-based Analysis of deep brain stimulation of the thalamus", Proceedings of the Second joint EMBS/BMES Conference, vol. 3, Annual Fall Meeting of the Biomedical Engineering Society (Cat. No. 02CH37392) IEEE Piscataway,NJ, (2002), 2047-2048.

Micheli-Tzanakou, E., et al., "Computational Intelligence for target assesment in Parkinson's disease", Proceedings of SPIE vol. 4479, Applications and Science of Neural Networks, Fuzzy Systems, and Evolutionary Computation IV, (2001), 54-69.

"Deep-brain stimulation of the subthalamic nucleus or the pars interna of the globus pallidus in Parkinson's disease", N Engl J Med., 345(13), Author: Deep-Brain Stimulation for Parkison's Disease Study Group, (Sep. 27, 2001), 956-963.

"International Search Report and Written Opinion for Application No. PCT/US2005/023672, date mailed Jan. 20, 2006", 19 pages.

Adler, D. E., et al., "The tentorial notch: anatomical variation, morphometric analysis, and classification in 100 human autopsy cases", J. Neurosurg. 96(6), (Jun. 2002), 1103-1112.

Alexander, D. C., et al., "Spatial transformations of diffusion tensor magnetic resonance images", IEEE Transactions on Medical Imaging, 20(11), (2001) 1131-1139.

Alo, K. M., et al., "New trends in neuromodulation for the management of neuropathic pain", Neurosurgery, 50(4), (Apr. 2002), 690-703; discussion 703-4.

Ashby, R, et al., "Neurophysiological effects of stimulation through electrodes in the human subthalamic nucleus", Brain, 122 (Pt 10), (Oct. 1999), 1919-1931.

Baker, K. K B. et al., "Subthalamic nucleus deep brain stimulus evoked potentials: Physiological and therapeutic implications", Movement Disorders, 17(5), (Sep./Oct. 2002), 969-983.

Bammer, R., et al., "Diffusion tensor imaging using single-shot SENSE-EPI", Magn Reson Med., 48(1), 48(1), (Jul. 2002), 128-136.

Basser, P. J., et al., "MR diffusion tensor spectroscopy and imaging", Biophys J., 66(1), (Jan. 1994), 259-267.

Basser, P. J., et al., "New currents in electrical stimulation of excitable tissues", Annu Rev Biomed Eng., 2, (2000), 377-397.

Benabid, A. L, et al., "Chronic electrical stimulation of the ventralis intermedius nucleus of the thalamus as a treatment of movement disorders", J. Neurosurg., 84(2), (Feb. 1996), 203-214.

Benabid, A. L, et al., "Combined (thalamotoy and stimulation) stereotactic surgery of the VIM thalamic nucleus for bilateral Parkinson disease", Appl Neurophysiol, vol. 50, (1987), 344-346.

Benabid, A. L, et al., "Long-term suppression of tremor by chronic stimulation of the ventral intermediate thalamic nucleus", Lancet, 337 (8738), (Feb. 16, 1991), 403-406.

Christensen, Gary E., et al., "Volumetric transformation of brain anatomy", IEEE Transactions on Medical Imaging, 16 (6), (Dec. 1997), 864-877.

Cooper, S, et al., "Differential effects of thalamic stimulation parameters on tremor and paresthesias in essential tremor", Movement Disorders, 17(Supp. 5), (2002), S193.

Coubes, R, et al., "Treatment of DYT1-generalised dystonia by stimulation of the internal globus pallidus", Lancet, 355 (9222), (Jun. 24, 2000), 2220-2221.

Finnis, K. W., et al., "3-D functional atalas of subcortical structures for image guided stereotactic neurosurgery", Neuroimage, vol. 9, No. 6, Iss. 2, (1999), S206.

Finnis, K. W., et al., "3D Functional Database of Subcortical Structures for Surgical Guidance in Image Guided Stereotactic Neurosurgery", Medical Image Computing and Computer-Assisted Intervention—MICCAI'99, Second International Conference, Cambridge, UK, Sep. 19-22, 1999, Proceedings, (1999), 758-767.

Finnis, K. W., et al., "a 3-Dimensional Database of Deep Brain Functional Anatomy, and its Application to Image-Guided Neurosurgery", Proceedings of the Third International Conference on Medical Image Computing and Computer-Assisted Intervention, Lecture Notes in Computer Science; vol. 1935, (2000), 1-8.

Finnis, K. W., et al., "A functional database for guidance of surgical and therapeutic procedures in the deep brain",Proceedings of the 22nd Annual International Conference of the IEEE Engineering in Medicine and Biology Society, vol. 3, (2000),1787-1789.

Finnis, K. W., et al., "Application of a Population Based Electrophysiological Database to the Planning and Guidance of Deep Brain Stereotactic Neurosurgery", Proceedings of the 5th International Conference on Medical Image Computing and Computer-Assisted Intervention-Part II, Lecture Notes in Computer Science; vol. 2489, (2002), 69-76.

Finnis, K. W., et al., "Subcortical physiology deformed into a patient-specific brain atlas for image-guided stereotaxy", Proceedings of SPIE—vol. 4681 Medical Imaging 2002: Visualization, Image-Guided Procedures, and Display, (May 2002), 184-195.

Finnis, Kirk W., et al., "Three-Dimensional Database of Subcortical Electrophysiology for Image-Guided Stereotatic Functional Neurosurgery", IEEE Transactions on Medical Imaging, 22(1), (Jan. 2003), 93-104.

Gabriels, L., et al., "Deep brain stimulation for treatment-refractory obsessive-compulsive disorder: psychopathological and neuropsychological outcome in three cases", Acta Psychiatr Scand., 107(4), (2003), 275-282.

Gabriels, L. A., et al., "Long-term electrical capsular stimulation in patients with obsessive-compulsive disorder", Neurosurgery, 52(6), (Jun. 2003), 1263-1274.

Goodall, E. V., et al., "Modeling study of activation and propagation delays during stimulation of peripheral nerve fibers with a tripolar cuff electrode", IEEE Transactions on Rehabilitation Engineering, [see also IEEE Trans. On Neural Systems and Rehabilitation], 3(3), (Sep. 1995), 272-282.

Goodall E. V., et al., "Position-selective activation of peripheral nerve fibers with a cuff electrode", IEEE Transactions on Biomedical Engineering, 43(8), (Aug. 1996), 851-856.

Goodall, E. V., et al., "Simulation of activation and propagation delay during tripolar neural stimulation", Proceedings of the 15th Annual International Conference of the IEEE Engineering in Medicine and Biology Society, (1993), 1203-1204.

Grill, W M., "Modeling the effects of electric fields on nerve fibers: influence of tissue electrical properties", IEEE Transactions on Biomedical Engineering, 46(8), (1999), 918-928.

Grill, W. M., et al., "Neural and connective tissue response to long-term implantation of multiple contact nerve cuff electrodes", J Biomed Mater Res., 50(2), (May 2000), 215-26.

Grill, W. M., "Neural modeling in neuromuscular and rehabilitation research", Proceedings of the 23rd Annual International Conference of the IEEE Engineering in Medicine and Biology Society, vol. 4, (2001), 4065-4068.

Grill, W. M., "Non-invasive measurement of the input-output properties of peripheral nerve stimulating electrodes", Journal of Neuroscience Methods, 65(1), (Mar. 1996), 43-50.

Grill, W. M., "Quantification of recruitment properties of multiple contact cuff electrodes", IEEE Transactions on Rehabilitation Engineering, [see also IEEE Trans. On Neural Systems and Rehabilitation], 4(2), (Jun. 1996), 49-62.

Grill, W. M., "Spatially selective activation of peripheral nerve for neuroprosthetic applications", Ph.D, Case Western Reserve University, (1995), 245 pages.

Grill, W. M., "Stability of the input-output properties of chronically implanted multiple contact nerve cuff stimulating electrodes", IEEE Transactions on Rehabilitation Engineering [see also IEEE Trans. on Neural Systems and Rehabilitation], (1998), 364-373.

Grill, W. M., "Stimulus waveforms for selective neural stimulation", IEEE Engineering in Medicine and Biology Magazine, 14(4), (Jul.-Aug. 1995). 375-385.

Grill, W. M., "Temporal stability of nerve cuff electrode recruitment properties", IEEE 17th Annual Conference Engineering in Medicine and Biology Society, vol. 2, (1995), 1089-1090.

Gross, R E., et al., "Advances in neurostimulation for movement disorders", Neurol Res., 22(3), (Apr. 2000), 247-258.

Haberler, C., et al., "No tissue damage by chronic deep brain stimulation in Parkinson's disease", Ann Neurol., 48(3), (Sep. 2000), 372-376.

Hamel, W., et al., "Deep brain stimulation of the subthalamic nucleus in Parkinson's disease: evaluation of active electrode contacts", J Neurol Neurosurg Psychiatry, 74(8), (Aug. 2003), 1036-1046.

Haueisen, J., et al., "The influence of brain tissue anisotropy on human EEG and MEG", Neuroimage, 15(1), (Jan. 2002), 159-166.

Hodaie, M., et al., "Chronic anterior thalamus stimulation for intractable epilepsy", Epilepsia, 43(6), (Jun. 2002), 603-608.

Hoekema, R., et al., "Multigrid solution of the potential field in modeling electrical nerve stimulation", Comput Biomed Res., 31(5), (Oct. 1998), 348-62.

Holsheimer, J., et al., "Identification of the target neuronal elements in electrical deep brain stimulation", Eur J Neurosci., 12(12), (Dec. 2000), 4573-7.

Jezernik, S., et al., "Neural network classification of nerve activity recorded in a mixed nerve", Neurol Res., 23(5), (Jul. 2001), 429-34.

Jones, D. K et al., "Optimal strategies for measuring diffusion in anisotropic systems by magnetic resonance imaging", Magn. Reson. Med., 42(3), (Sep. 1999), 515-525.

Krack, P., et al., "Postoperative management of subthalamic nucleus stimulation for Parkinson's disease", Mov. Disord., vol. 17(suppl 3), (2002), 188-197.

Le Bihan, D., et al., "Diffusion tensor imaging: concepts and applications", J Magn Reson Imaging, 13(4), (Apr. 2001), 534-546.

Lee, D. C., et al., "Extracellular electrical stimulation of central neurons: quantitative studies", In: Handbook of neuroprosthetic methods, WE Finn and PG Lopresti (eds) CRC Press, (2003), 95-125.

Levy, A. L., et al., "An Internet-connected, patient-specific, deformable brain atlas integrated into a surgical navigation system", J Digit Imaging, 10(3 Suppl 1), (Aug. 1997), 231-237.

McIntyre, Cameron C., et al., "Cellular effects of deep brain stimulation model-based analysis of activation and inhibition", J Neurophysiol, 91(4), (Apr. 2004), 1457-1469.

McIntyre' Cameron C., et al., "Electric field generated by deep brain stimulation of the subthalamic nucleus", Biomedical Engineering Society Annual Meeting, Nashville TN, (Oct. 2003).

McIntyre, Cameron C., et al., "Extracellular stimulation of central neurons: influence of stimulus waveform and frequency on neuronal output", J. Neurophysiol., 88(4), (Oct. 2002), 1592-1604.

McIntyre, C. C., et al., "Microstimulation of spinal motoneurons: a model study", Proceedings of the 19th Annual International Conference of the IEEE Engineering in Medicine and Biology society, vol. 5, (1997), 2032-2034.

McIntyre, C. C., et al., "Model-based design of stimulus trains for selective microstimulation of targeted neuronal populations", Proceedings of the 23rd Annual International Conference of the IEEE Engineering in Medicine and Biology Society, vol. 1, (2001), 806-809.

McIntyre, C. C., et al., "Model-based design of stimulus waveforms for selective microstimulation in the central nervous system", Proceedings of the First Joint [Engineering in Medicine and Biology, 1999. 21st Annual Conf. and the 1999 Annual FallMeeting of the Biomedical Engineering Soc.] BMES/EMBS Conference, vol. 1, (1999), 384.

McIntyre, Cameron C., et al., "Modeling the excitability of mammalian nerve fibers: influence of afterpotentials on the recovery cycle", J Neurophysiol, 87(2), (Feb. 2002), 995-1006.

McIntyre, Cameron C., et al., "Selective microstimulation of central nervous system neurons", Annals of biomedical engineering, 28(3), (Mar. 2000), 219-233.

McIntyre, C. C., et al., "Sensitivity analysis of a model of mammalian neural membrane", Biol Cybern., 79(1), (Jul. 1998), 29-37.

McIntyre, Cameron C., et al., "Uncovering the mechanism(s) of action of deep brain stimulation: activation, inhibition, or both.", Clin Neurophysiol, 115(6), (Jun. 2004), 1239-48.

McIntyre, Cameron C., et al., "Uncovering the mechanism(s) of deep brain stimulation for Parkinson's disease through functional imaging, neural recording, and neural modeling", Crit Rev Biomed Eng., 30(4-6), (2002), 249-281.

McNeal, D. R., et al., "Analysis of a model for excitation of myelinated nerve", IEEE Trans Biomed Eng., vol. 23, (1976), 329-337.

Miocinovic, S., et al., "Sensitivity of temporal excitation properties to the neuronal element activated by extracellular stimulation", J Neurosci Methods, 132(1), (Jan. 15, 2004), 91-9.

Moffitt, M. A., et al., "Prediction of myelinated nerve fiber stimulation thresholds: limitations of linear models", IEEE Transactions on Biomedical Engineering, 51(2), (2003), 229-236.

Moro, E., et al., "The impact on Parkinson's disease of electrical parameter settings in STN stimulation", Neurology, 59 (5), (Sep. 10, 2002), 706-713.

Nowak, L. G., et al., "Axons, but not cell bodies, are activated by electrical stimulation in cortical gray matter. I. Evidence from chronaxie measurements", Exp. Brain Res., 118(4), (Feb. 1998), 477-488.

Nowak, L. G., et al., "Axons, but not cell bodies, are activated by electrical stimulation in cortical gray matter. II. Evidence from selective inactivation of cell bodies and axon initial segments", Exp. Brain Res., 118(4), (Feb. 1998), 489-500.

O'Suilleabhain, P. E., et al., "Tremor response to polarity, voltage, pulsewidth and frequency of thalamic stimulation", Neurology, 60(5), (Mar. 11, 2003), 786-790.

Pierpaoli, C., et al., "Toward a quantitative assessment of diffusion anisotropy", Magn Reson Med., 36(6), (Dec. 1996), 893-906.

Plonsey, R., et al., "Considerations of quasi-stationarity in electrophysiological systems", Bull Math Biophys., 29(4), (Dec. 1967), 657-664.

Ranck, J. B., "Specific impedance of rabbit cerebral cortex", Exp. Neurol., vol. 7, (Feb. 1963), 144-152.

Ranck, J. B., "The Specific impedance of the dorsal columns of the cat: an anisotropic medium", Exp. Neurol., 11, (Apr. 1965), 451-463.

Ranck, J. B., "Which elements are excited in electrical stimulation of mammalian central nervous system: a review", Brain Res., 98(3), (Nov. 21, 1975), 417-440.

Rattay, F., et al., "A model of the electrically excited human cochlear neuron. I. Contribution of neural substructures to the generation and propagation of spikes", Hear Res., 153(1-2), (Mar. 2001), 43-63.

Rattay, F., "A model of the electrically excited human cochlear neuron. II. Influence of the three-dimensional cochlear structure on neural excitability", Hear Res., 153(1-2), (Mar. 2001), 64-79.

Rattay, F., "Arrival at Functional Electrostimulation by modelling of fiber excitation", Proceedings of the Ninth annual Conference of the IEEE Engineering in Medicine and Biology Society, (1987), 1459-1460.

Rattay, F., "The influence of intrinsic noise can preserve the temporal fine structure of speech signals in models of electrically stimulated human cochlear neurones", Journal of Physiology, Scientific Meeting of the Physiological Society, LondonEngland, UK Apr. 19-21, 1999, (Jul. 1999), 170P.

Rizzone, M. et al., "Deep brain stimulation of the subthalamic nucleus in Parkinson's disease: effects of variation in stimulation parameters", J. Neurol. Neurosurg. Psychiatry, 71(2), (Aug. 2001), 215-219.

Saint-Cyr, J. A., et al., "Localization of clinically effective stimulating electrodes in the human subthalamic nucleus on magnetic resonance imaging", J. Neurosurg., 87(5), (Nov. 2002), 1152-1166.

Sances, A., et al., "In Electroanesthesia: Biomedical and Biophysical Studies", A Sances and SJ Larson, Eds., Academic Press, NY, (1975), 114-124.

St. Jean, P., et al., "Automated atlas integration and interactive three-dimensional visualization tools for planning and guidance in functional neurosurgery", IEEE Transactions on Medical Imaging, 17(5), (1998), 672-680.

Starr, P. A., et al., "Implantation of deep brain stimulators into the subthalamic nucleus: technical approach and magnetic resonance imaging-verified lead locations", J. Neurosurg., 97(2), (Aug. 2002), 370-387.

Sterio, D., et al., "Neurophysiological refinement of subthalamic nucleus targeting", Neurosurgery, 50(1), (Jan. 2002), 58-69.

Struijk, J. J., et al., "Excitation of dorsal root fibers in spinal cord stimulation: a theoretical study", IEEE Transactions on Biomedical Engineering, 40(7), (Jul. 1993), 632-639.

Struijk, J. J., et al., "Recruitment of dorsal column fibers in spinal cord stimulation: influence of collateral branching", IEEE Transactions on Biomedical Engineering, 39(9), (Sep. 1992), 903-912.

Tamma, F., et al., "Anatomo-clinical correlation of intraoperative stimulation-induced side-effects during HF-DBS of the subthalamic nucleus", Neurol Sci., vol. 23 (Suppl 2), (2002), 109-110.

Tarler, M., et al., "Comparison between monopolar and tripolar configurations in chronically implanted nerve cuff electrodes", IEEE 17th Annual Conference Engineering in Medicine and Biology Society, vol. 2, (1995), 1093-1094.

Testerman, Roy L., "Coritical response to callosal stimulation: A model for determining safe and efficient stimulus parameters", Annals of Biomedical Engineering, 6(4), (1978), 438-452.

Tuch, D. S., et al., "Conductivity mapping of biological tissue using diffusion MRI", Ann N Y Acad Sci., 888, (Oct. 30, 1999), 314-316.

Tuch, D. S., et al., "Conductivity tensor mapping of the human brain using diffusion tensor MRI", Proc Natl Acad Sci U S A., 98(20), (Sep. 25, 2001), 11697-11701.

Veraart, C. , et al., "Selective control of muscle activation with a multipolar nerve cuff electrode", IEEE Transactions on Biomedical Engineering, 40(7), (Jul. 1993), 640-653.

Vercueil, L., et al., "Deep brain stimulation in the treatment of severe dystonia", J. Neurol., 248(8), (Aug. 2001), 695-700.

* cited by examiner

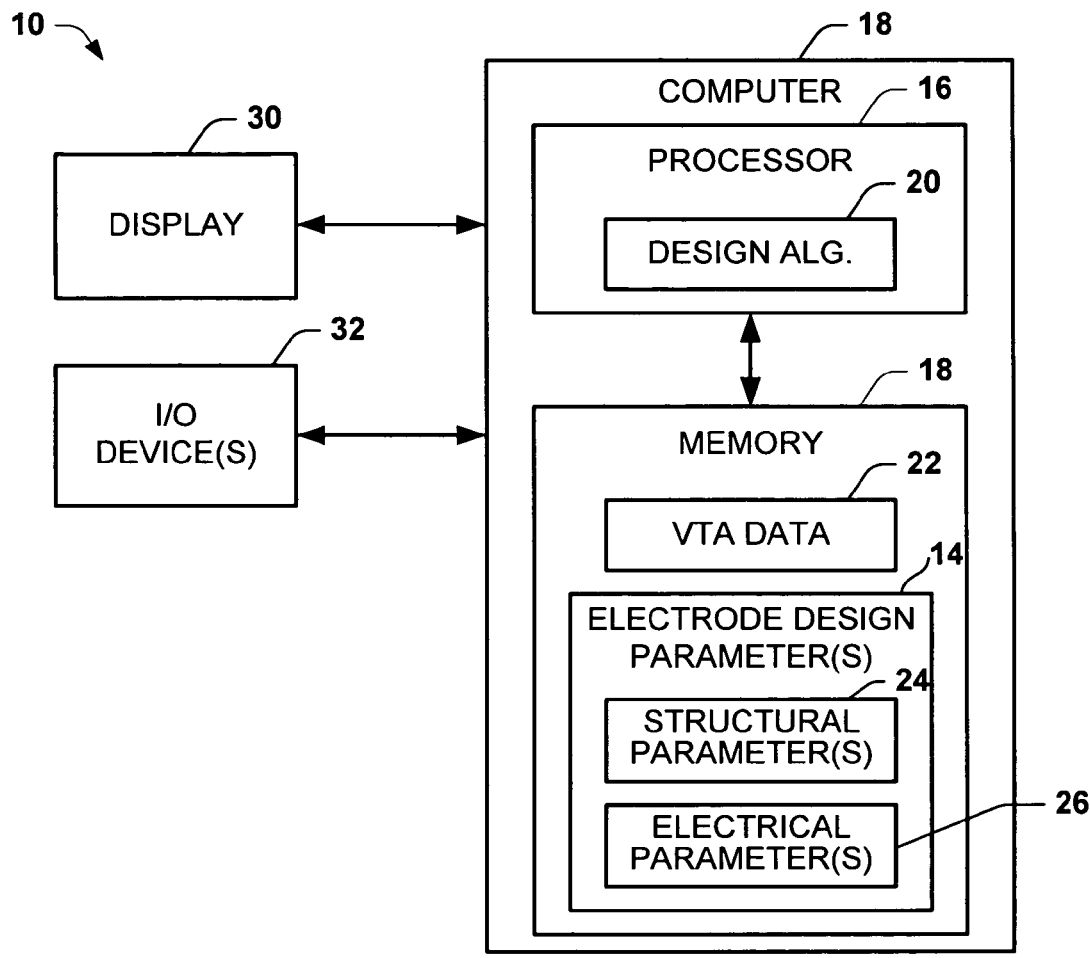
FIG. 1
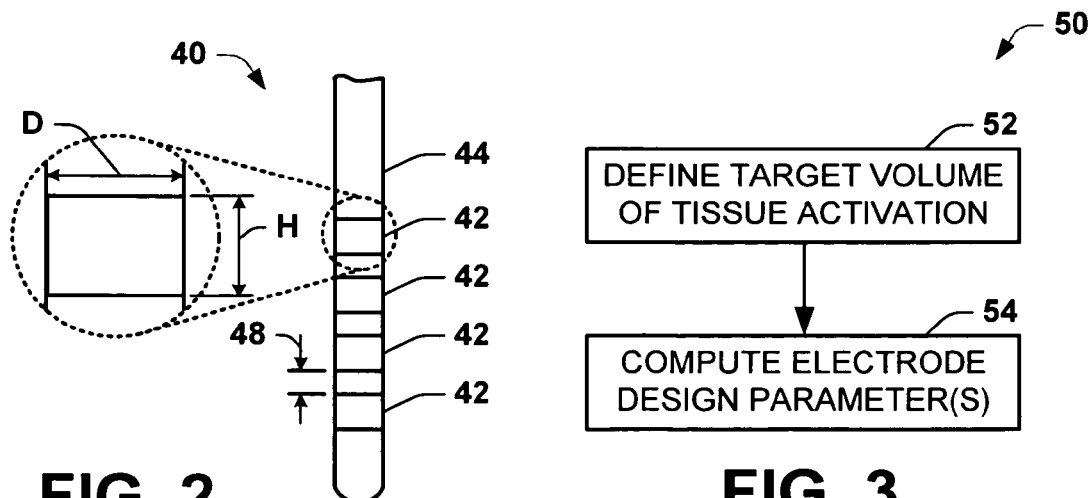
FIG. 2   FIG. 3

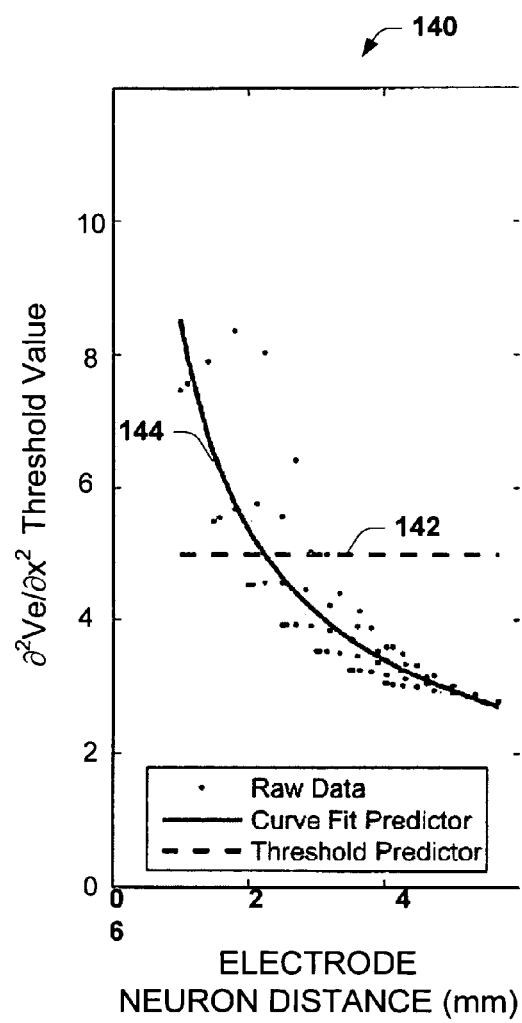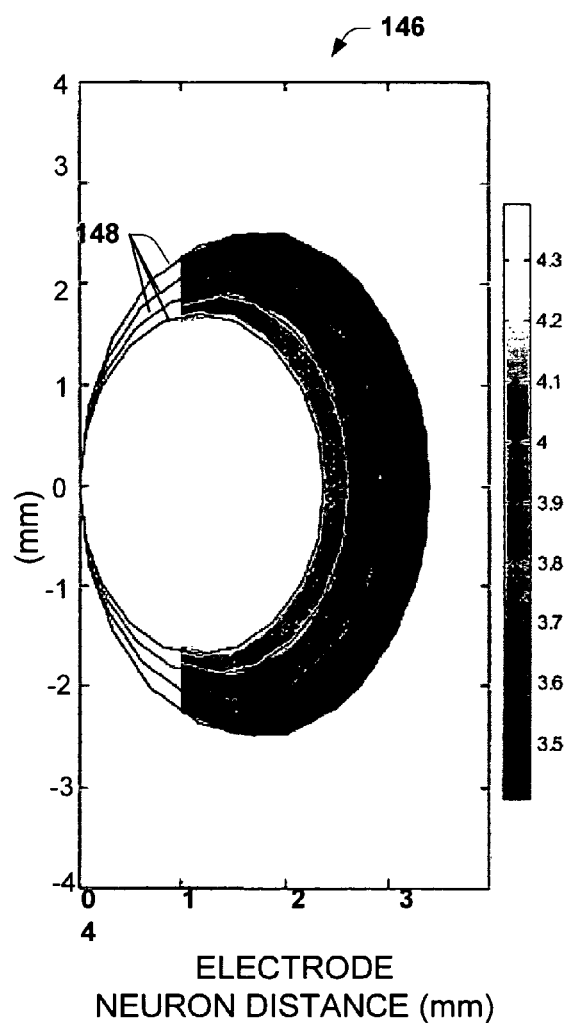
FIG. 5  FIG. 6

SYSTEM AND METHOD TO DESIGN STRUCTURE FOR DELIVERING ELECTRICAL ENERGY TO TISSUE

RELATED APPLICATIONS

This application is a continuation-in-part of U.S. patent application Ser. No. 10/885,982, which was filed Jul. 7, 2004, now U.S. Pat. No. 7,346,382 and entitled Brain Stimulation Models, Systems, and Methods, and claims the benefit of provisional patent application No. 60/740,031 which was filed on Nov. 28, 2005, and entitled "Role of electrode design on the volume of tissue activated during deep brain stimulation" the entire contents of both applications are incorporated herein by reference.

BACKGROUND

Electrical stimulation of the nervous system has provided a therapeutic treatment for a variety of disorders. For example, electrical stimulation has been applied to pain management, such as by performing stimulation of the spinal cord. Electrical stimulation has also been performed to augment hearing in the context of cochlear implants. Deep brain stimulation (DBS) has become an established therapy for treating various conditions including, for example, Parkinson's disease and dystonia. DBS has also been employed to treat several other conditions, such as clinical depression, obsessive compulsive disorder, and epilepsy to name a few.

By way of further example, the discovery that high frequency DBS generates clinical benefits analogous to those achieved by surgical lesioning has transformed the use of functional neurosurgery for the treatment of movement disorders. In first world countries, thalamic DBS for intractable tremor has replaced ablative lesions of the thalamus, and DBS of the subthalamic nucleus or globus pallidus internus (GPi). GPi has replaced pallidotomy in the treatment of the cardinal motor features of Parkinson's disease (e.g., tremor, rigidity, bradykinesia). In addition, GPi DBS has emerged as an effective therapy for dystonia, and the utility of DBS is being examined for the treatment of epilepsy, obsessive-compulsive disorder, Tourette's syndrome, and major depression.

Despite the documented clinical successes of neurostimulation, the mechanisms and effects of neurostimulation at the neuronal level remain difficult to predict. As a result, modeling and simulation have played increasingly important roles in the engineering design and scientific analysis of neurostimulation.

SUMMARY

The present invention relates systems and methods for designing an electrode to provide for stimulation of an anatomical region to achieve a desired therapeutic effect. According to an aspect of the invention, systems and methods can be employed to determine an electrode design that is customized to the anatomical and/or morphological features of an identified stimulation target. For instance, the systems and methods can be employed according to an aspect of the invention to determine electrode design parameters, which can include one or more of structural parameters (e.g., electrode height, diameter, and/or shape) and electrical parameters (e.g., voltage or current amplitude, frequency, pulse width or duration, and/or waveform shape).

One aspect of the invention provides a computer-assisted method that includes defining a target volume of tissue activation to achieve a desired therapeutic effect for an identified anatomic region. At least one parameter is computed for an electrode design as a function of the defined target volume of tissue activation. The computed parameter(s) can be stored in memory for the electrode design. The one or more parameters can be used to construct a custom electrode for treatment of a given disorder.

Another aspect of the invention provides a method for determining an electrode design. The method can include selecting an anatomical region to achieve a desired therapeutic effect and defining a target volume of tissue activation in the selected anatomical region expected to achieve the desired therapeutic effect. At least one electrode structure parameter and at least one stimulation parameter are determined to provide a design volume of tissue activation that substantially matches the target volume of tissue activation. The determined at least one electrode structure parameter and the at least one stimulation parameter can be stored, such as to define the electrode design.

Still another aspect of the invention provides a system to determine an electrode design. The system includes memory that stores data defining a target volume of tissue activation in an anatomical region expected to achieve a desired therapeutic effect. An optimization method determines a value of at least one electrode design parameter, which defines the electrode design, expected to provide a design volume of tissue activation that substantially matches the target volume of tissue activation.

BRIEF DESCRIPTION OF THE DRAWINGS

FIG. 1 depicts an example of a system that can be utilized to design an electrode according to an aspect of the invention.

FIG. 2 depicts a schematic example of an electrode that can be constructed from an electrode design according to an aspect of the invention.

FIG. 3 is a flow diagram of a general method that can be employed to design an electrode according to an aspect of the present invention.

FIG. 5 depicts a graph plotting thresholds that can be applied to predict neural stimulation.

FIG. 6 depicts a plot of a second difference-based approach that can be used to predict neural stimulation.

DETAILED DESCRIPTION

Figure 4:
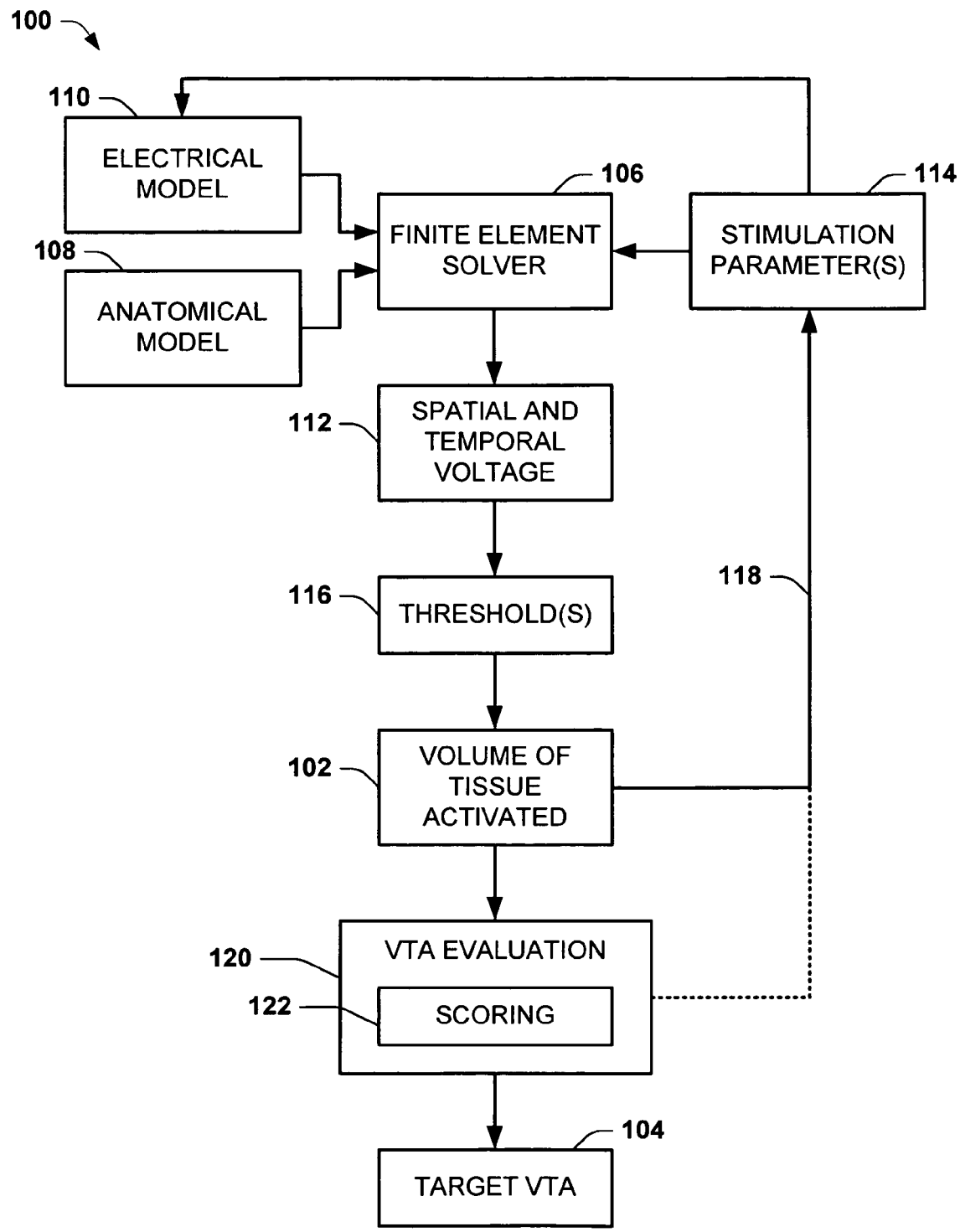
FIG. 4 depicts a functional block diagram of an example approach that can be employed to determine a volume of tissue activation according to an aspect of the invention.

The present invention relates to systems and methods that can be employed to ascertain an electrode design to achieve a target volume of tissue activation in an anatomical region (e.g., a nucleus) that is identified with a desired therapeutic effect. The anatomical region and target volume of tissue activation can vary according to the particular disorder being treated as well as the anatomic features of such region.

As one example, a common electrode design is currently used in most existing DBS applications, even though substantial morphological and anatomical differences exist between the various target nuclei in the brain. Differences can become more pronounced for neurostimulation applied to other anatomical structures, such as the spinal cord or peripheral nerves. Accordingly, the systems and methods described herein allow the design of one or more electrode parameters that can be employed to construct an electrode capable of achieving improved performance relative to many existing electrodes. For example, such an electrode can be customized for use in providing electrical stimulation to a desired anatomical site, such as a nucleus, identified for treatment of a particular disorder. Additionally or alternatively, the electrode design can be further customized for stimulating a target anatomical volume for a given patient.

Referring to FIG. 1, an example of a basic system 10 for determining an electrode design is illustrated. The system 10 is depicted as being implemented using a computer 12 that is programmed and/or configured to determine one or more electrode design parameters 14 according to an aspect of the invention. The computer 12 can be a workstation, a standalone computer, a notebook computer, or it can be implemented as part of a microprocessor-based appliance or other equipment available that is programmed based on the teachings contained herein.

The computer 12 includes a processor 16 that is operative to execute instructions for performing the methods described herein. The instructions can be stored in associated memory 18. In the example of FIG. 1, the processor 16 is depicted as running a design algorithm 20. Such design algorithm 20 can be stored in the memory 18 and loaded into the processor 16 for determining the electrode design. The design algorithm 20 can be programmed to determine one or more electrode design parameters 14 as a function of a target volume of tissue activation (VTA), as defined by VTA data 22.

As used herein, the target VTA represents an anatomical region in which neurons within such region are expected to be activated to achieve a desired therapeutic effect. Stated differently, the neurons within the VTA are expected to generate propagating action potentials at a stimulus frequency in response to electrical stimulation delivered at a stimulation electrode contact located within the VTA. While the phrase "volume of tissue activation" and its equivalents typically represents a volume of tissue activation of an anatomical region, it will be appreciated that such volume could also represent a volume of inhibition region or a volume of tissue deactivation, as the stimulation could result in either generation of an activation potential or the inhibition of existing activation potential.

The target VTA thus can be predefined for a given patient or a set of patients, such as for treating an identified disorder, and stored as the VTA data 22. Alternatively, the target VTA can be pre-computed for one or more known anatomical regions, which VTA can be warped or morphed to fit the corresponding anatomical region of a particular patient and stored to provide the target VTA data 20. As another alternative, a target VTA can be computed by the computer 10 (or another computer—not shown) and stored as the VTA data 20. Some example approaches that can be employed to determine the target VTA are described herein (see, e.g., FIG. 4). As one example, the target VTA can correspond to a probabilistic definition of the anatomical volume in an identified anatomical region derived from clinical tests performed on a statistically significant population. These and other examples of how a VTA and, in particular, a target VTA can be determined are described in the above-incorporated U.S. patent application Ser. No. 10/885,982. Those skilled in the art will understand and appreciate other ways in which the VTA data 22 can be generated and stored for use by the system 10.

The electrode design parameters 14 computed by the design algorithm 20 can include electrode structural (or morphological) parameters 24, electrode stimulation parameters 26 or a combination of structural and stimulation parameters. For the example of an electrode having a cylindrical electrode contact, the electrode structural parameters 24 can include the height and/or diameter of each cylindrical electrode contact. For an electrode having one or more contacts that are spaced apart from each other along the electrode shaft, the structural parameters 24 can also include an axial spacing between electrode pairs. It will be understood and appreciated that the electrode contacts can have other shapes than a circular cylindrical shape. For example, an electrode contacts can have a substantially C-shaped cross-section, such that the electrode structural parameters 24 can include the radius of curvature, the arc length, and/or an axial length of the contact. Thus, the arc length thus can range from zero degrees (corresponding to no contact) up to 360 degrees (corresponding to a cylindrical type of contact). The electrode structural parameters 24 can include other geometric features (e.g., shape, contours, discontinuities, and the like) and interrelationships for the contacts that form the electrode.

The electrode stimulation parameters 26 can also be determined by the design algorithm 20 to achieve a desired therapeutic effect by providing electrical stimulation to a target VTA.

Those skilled in the art will understand and appreciate various optimization methods that can be utilized by the design algorithm 20 to determine the structural parameters and/or the electrical parameters for the electrode design for approximating the target VTA. For example, in some cases it may be sufficient to ascertain the structural parameter(s) 24 over a predefined set of stimulation parameters 26 during a first optimization routine. The stimulation parameters 26 can be fine tuned during a second optimization routine. Alternatively, the structural parameters 24 and the electrical parameters 26 can form a parameter space that is optimized collectively. The order and interrelationship between the stimulation parameters and the structural parameters thus can be optimized to achieve or approximate a desired therapeutic effect to varying degrees of specificity and according to what approximations and assumptions are made during such analysis. Additionally, the resulting parameters 14 can be determined to accommodate anatomical variability between patients as well as potential surgical variability associated with implantation of the electrode to a target implantation site. The electrode design parameters 24 further can be ascertained to provide electrode contact dimensions that maximize the stimulation influence while keeping charge injection levels to a minimum.

The system 10 can also include a display 30 that can be utilized to represent the results and calculations performed by the design algorithm. For instance, the display can demonstrate a graphical representation, textual representation or a combination graphical and textual information associated with determining an electrode design. As one example, a graphical interface can provide data to the display 30 for overlaying an expected VTA for one or more given designs over the target VTA. Such a representation provides a visual demonstration of expected performance that can help determine which design parameters should be utilized to construct an electrode for given situation.

The system 10 can also include one or more other input or output devices 32. Such devices 32 can provide an interface through which a user can input data as well as control the design algorithm 20. For example, a user can employ the I/O device 32 to input data, such as instructions to initiate or modify the electrode design procedure. Alternatively, the I/O device can be employed to acquire the VTA data 22, such as from another location in the memory 18, from another storage location, or to acquire the VTA data from another process running on the computer 12 on another machine. A user can also employ the I/O device 32 to set the range of parameters 14, the granularity of such parameters as well as to program other parameters being used in the procedure. The I/O device 32 can also be utilized to interface and enable acquisition of data (e.g., imaging data) from an associated imaging device, such as a magnetic resonance imaging (MRI) system, a computer tomography (CT) system or other imaging modality.

As another example, the I/O device 32 can correspond to an implantable pulse generator (or other stimulation equipment). The computer 18 can program the I/O device 32 based on the stimulation parameters 26 determined to achieve maximal VTA coverage relative to the target VTA for the electrode design. In this way, a custom-designed electrode (constructed according to the electrode structural parameters 24) can be operated with appropriate stimulation parameters, to achieve stimulation that substantially matches the target VTA. It will be understood and appreciated that the system 10 thus can be employed to determine an electrode design (e.g., including structural and electrical stimulation parameters) that can achieve a VTA with increased specificity. Thus, the systems and methods described herein will facilitate more accurate neurostimulation.

FIG. 2 depicts a schematic example of part of an electrode 40 that can be constructed based on design parameters determined according to an aspect of the invention. The electrode 40 can include one or more contacts 42 that are spaced axially apart from each other along an elongated shaft 44 of the electrode. In the example of FIG. 2, each of the contacts 42 is depicted as a cylinder having a height (H) and a diameter (D), such as can be determined as part of an electrode design according to an aspect of the invention. The relationship between height and diameter can be characterized as an aspect ratio (d/h), which itself can also be a design parameter. It will be understood that the electrode contacts 42 can have the same diameter and height or the diameter and height can vary among the contacts. Thus, various combinations exist that can provide for the same or different surface area for each of the contacts 42.

As shown in the enlarged portion of the electrode 40, the height of the electrode contact 42 is defined by the distance between axially spaced apart edges 44 and 46. While the edges are depicted as being annular edges, other shapes (e.g., sinusoidal, saw tooth, and the like) can also be provided at the respective edges 44 and 46. Each contact also has a diameter, which is fixed for a substantially right-circular cylindrical electrode configuration. Other shapes and configurations could also be utilized, which may or may not be cylindrical. As mentioned above, the electrode design algorithm 20 (FIG. 1) can also determine the spacing 48 between adjacent pairs of the electrode contacts 42. The spacing 48 between the adjacent pairs of the electrode contacts 42 can be different or it can be the same. Thus, the structural parameters of the electrode 40 can vary depending on the dimensions and configuration of the target VTA for the intended target location of the electrode. While the example of FIG. 2 has been described in the context of plural cylindrical electrode contacts, it will be understood that, as described herein, the systems and methods of the present invention are not limited to any particular electrode geometry. Instead, the approach described herein allows for any shape and configuration and dimension of electrode contact(s) to be deigned for providing electrical stimulation that can achieve a target VTA for achieving a desired therapeutic effect.

A general method 50 that can be employed to determine an electrode design according to an aspect of the invention is depicted in FIG. 3. The method includes defining a target VTA, indicated at 52. As described herein, the target VTA can be defined by pre-computing a VTA for treatment of a particular disorder, such as can be based on data acquired for one or more patients, or for a given patient according to such patient's condition. At 54, one or more electrode design parameters are computed. The electrode design parameters can include structural parameters, electrical parameters or a combination of structural and electrical parameters. The method 50, as well as variations thereof, can be implemented by a computer programmed accordingly. The method 50 can be performed automatically or portions of the method can which can include selection and acts performed by one or more persons. The method 50, as well as variations thereof, can also be embodied in a computer-readable medium, such as can be stored in memory of a computer or computer appliance, or be stored on an article of manufacture. Variations of this method 50 will be better appreciated with reference to other parts and embodiments provided in this description, including with respect to FIG. 1 and the following other FIGS. 4-20.

FIG. 4 depicts an example of a function block diagram of a system 100 that can be employed to determine a VTA 102 according to an aspect of the present invention. The system 100 can be implemented on a computer or workstation programmed to perform the methods and functions represented in and described with respect to FIG. 4. The system 100 further can be performed to calculate a target VTA 104 for achieving a desired therapeutic effect. For instance the target VTA 104 defines an anatomic region for stimulation that is expected to achieve a desired therapeutic effect, such as by generating propagating action potentials in response to electrical stimulation by one or more electrode contacts located within or near the target VTA. As described herein, the target VTA 104 can be utilized to compute one or more electrode geometry parameters (e.g., height, diameter, contact spacing, shape) and stimulation parameters (voltage or current, frequency, pulse width, and waveform shape) for an electrode design.

The system 100 of FIG. 4 includes a finite element model (FEM) solver 106 that is programmed and/or configured to determine a spatial and temporal voltage solution 112 based on anatomical and electrical models 108 and 110, respectively. The spatial and temporal voltage solution 112 can also vary according to stimulation parameters 114. For example, the FEM solver 106 can determine a spatial and temporal voltage solution 112 for each (or a subset) of the available stimulation parameters 114 based on the models 108 and 110.

The anatomical model 108 defines the location of the electrode as well as structural features of the anatomical region being modeled for use in the system 100. The anatomical model 108 can be generated using a suitable imaging modality (e.g., MRI or CT imaging), which can be utilized to define the electrode location in the anatomical region and the surrounding anatomical structures. For instance, the preliminary initial contact location can be at the anatomic center of the nucleus. The anatomical model 108 is coupled to the electrical model 110 that characterizes the electric field generated in the anatomical region. The electrical model 110, for example, can characterize tissue conductivity in the anatomical region of interest. As one example, the electrical model 110 can represent the tissue conductivity of the region as being isotropic and homogeneous. As another example the electrical model 110 can characterize the tissue conductivity as being anisotropic and inhomogeneous. The particular characterization can vary according to the desired accuracy and the particular type of tissue being represented by the anatomical and electrical models. The electrical model 110 can also characterize the electrical properties of the tissue electrode interface as well as the electrode impedance and the electrode capacitance. The electrical model 110 further can reflect the time dependence characteristics at the electrode tissue interface (e.g., via Fourier FEM), such as due to the electrode capacitance.

By way of example, many electrodes (e.g., as used for DBS) are three-dimensional structures and the tissue conductivity of the central nervous system is both inhomogeneous (dependent on location) and anisotropic (dependent on direction). The tissue inhomogeneity and anisotropy surrounding the electrode can alter the shape of the electric field and the subsequent neural response to stimulation. The anisotropy and inhomogeneity of such tissue medium can be accounted for by the FEM solver 106 and the electrical model 110 incorporating 3D tissue conductivities of the tissue. As one example, diffusion tensor imaging (DTI) can be employed to estimate an electrical conductivity tensor of the tissue medium surrounding one or more electrodes.

For instance, diffusion tensor imaging (DTI) can be employed to characterize the diffusional behavior of water in tissue on a voxel-by-voxel basis in terms of a matrix quantity from which the diffusion coefficient can be obtained corresponding to any direction in space. The electrical conductivity tensor ($\sigma$) of a tissue medium is obtainable from the corresponding diffusion tensor (D) determined for the tissue medium. The hypothesized relationship between electrical conductivity and water diffusion in tissue is prompted by the observation that in a structured medium the two processes are related through mutual respect for the boundary conditions imposed by the tissue geometry. It has been determined that a value of the electrical conductivity tensor $\sigma$ can be obtained for each voxel (e.g., from DTI data) using a linear transform of the matrix D:

$$\sigma = (\sigma_e/d_e)D \qquad \text{Equation 1}$$

where $\sigma_e$ is the effective extracellular conductivity, and $d_e$ is the effective extracellular diffusivity. The diffusion tensors obtained from a corresponding DTI modality can be transformed to conductivity tensors, as discussed above, and incorporated into the electrical model 110 and the FEM solver 106.

The FEM solver 106 thus can solve for the spatial and temporal voltage distribution (e.g., a potential distribution ($V_e$)) 112 that is generated in the tissue medium in response to electrical stimulation in the tissue according to the stimulation parameters 114. The unit of potential distribution can correspond to a single voxel, which can represent a pixel or a set of plural. For example, the FEM 106 solver can determine the potential distribution 112 in the anatomical region of tissue, which can vary according to the tissue model utilized by the FEM solver 106. The potential distribution 112 thus can represent the electric field for each voxel for predefined electrode contact geometry and stimulation parameters. As one example, the FEM solver 106 can be implemented as a Fourier FEM solver that accounts for the capacitance of the electrode-tissue interface under voltage-controlled stimulation. The FEM solver thus can incorporate the DTI-based tissue conductivities and the reactive components of the electrode-tissue interface into a single system of equations.

One or more thresholds 116 can be applied to the potential distribution 112 to ascertain (or predict) whether an activation potential has been achieved for each given unit (e.g., voxel) of the potential distribution. The thresholds 116 can be predefined and applied to the potential distribution 112 to determine a corresponding VTA 102 according to whether a corresponding activating potential has been achieved for each voxel. The VTA 102 can be computed for a defined set of stimulation parameters 114, such that a plurality of VTAs 102 can be determined to define a corresponding search space. The system 100 can recompute the VTA 102 (and appropriate intermediate values) for each set of stimulation parameters, which procedure is schematically represented by connection 118. That is, a corresponding search space of VTAs 102 can be determined over a range of stimulation parameters 114. The resulting search space of VTAs 102 can be analyzed by an optimization method 120 to ascertain the target VTA 104.

The thresholds 116 can be implemented by employing a neurostimulation predictor that ascertains whether a corresponding activating potential has been reached for. As one example, a Fourier FEM DBS electrode model can be coupled to an axon or neuron model (e.g., a field-neuron model) for the anatomical region to determine whether an activation potential exists for each voxel. Appropriate thresholds 116 can be defined for the axon or neuron model sufficient to trigger an activating potential in the aggregate FEM analysis.

An alternative approach to the field-neuron simulations described above is the use of an activating function-based technique. One example of such an activating function that can be employed to approximate the neuron response to electrical stimulation is a second difference of the extracellular potential distribution along a neural process ($\partial^2 V_e/\partial x^2$), where $V_e$ represents the potential of a given voxel. The second difference provides a quantitative estimate of the polarization of the axon or neuron in response to an applied electric field.

The second difference thus can be applied to the potential distribution to define 3D surfaces that encompass the volume, where $\partial^2 Ve/\partial x^2$ is suprathreshold for axonal activation for the given stimulation parameters 114.

By way of illustration, FIG. 5 depicts a graph that includes an example of $\partial^2 Ve/\partial x^2$ function that can be utilized as a predictor of neural activation. In the example of FIG. 5, the $\partial^2 Ve/\partial x^2$ values are plotted as a function of electrode-axon distance measured from the center of the electrode. An absolute threshold (indicated by a dashed line 142) is one type of simple predictor that can provide a low level of accuracy in predicting neural activation. An alternative approach is to perform a curve fitting function to provide a corresponding variable threshold (indicated by solid line 144) that approximates clinical raw data.

Yet another alternative approach is to determine the $\partial^2 Ve/\partial x^2$ threshold values as a function of pulse width and voltage. Specifically, $\partial^2 Ve/\partial x^2$ threshold values are recorded, and these values are expressed as a function of cathodic voltage (V) times pulse width (PW, µs). This expression allows two stimulation parameters to be condensed into a single number for prediction of thresholds. Further, threshold values recorded this way were found to be valid for a wide range of electrode designs and stimulation parameters. These values can then be used to create 2D spatial contours that are swept around the z-axis to define the VTA volume. For purposes of volume calculations, it is often convenient to describe the VTA contours with analytical functions. For example, each contour can be described by an ellipse:

$$(x-x0)^2/a2+(y-y0)^2/b2=1 \quad \text{Equation 2}$$

where x0, y0 is the center of the ellipse, and
a and b are the semimajor and semiminor axes, respectively (assuming b<a).

The semimajor and semiminor coefficients are calculated from the following: a=distance of threshold value from electrode contact along x-axis; b=maximum y value of 2D threshold contour. Under the model conditions used in this study, the electrode contact is centered on the origin and the center of each ellipse is x0=a, y0=0. With this method, $\partial^2 Ve/\partial x^2$ threshold values and VTA volumes can be predicted for a wide range of electrode designs and stimulation parameters.

FIG. 6 depicts an example of spatial ellipsoid-based predictors 148 that can be implemented as described above. The predictors 148 can be applied to a variety of electrode design and stimulation parameters. In the example of FIG. 6, corresponding $\partial^2 Ve/\partial x^2$ predictors for voltage-controlled stimulation are overlaid on filled $\partial^2 Ve/\partial x^2$ threshold contours, as represented by the associated indicator bar located to the right of the figure. The $\partial^2 Ve/\partial x^2$ threshold contours can be generated from the integrated field neuron model, as described herein.

Figure 7:
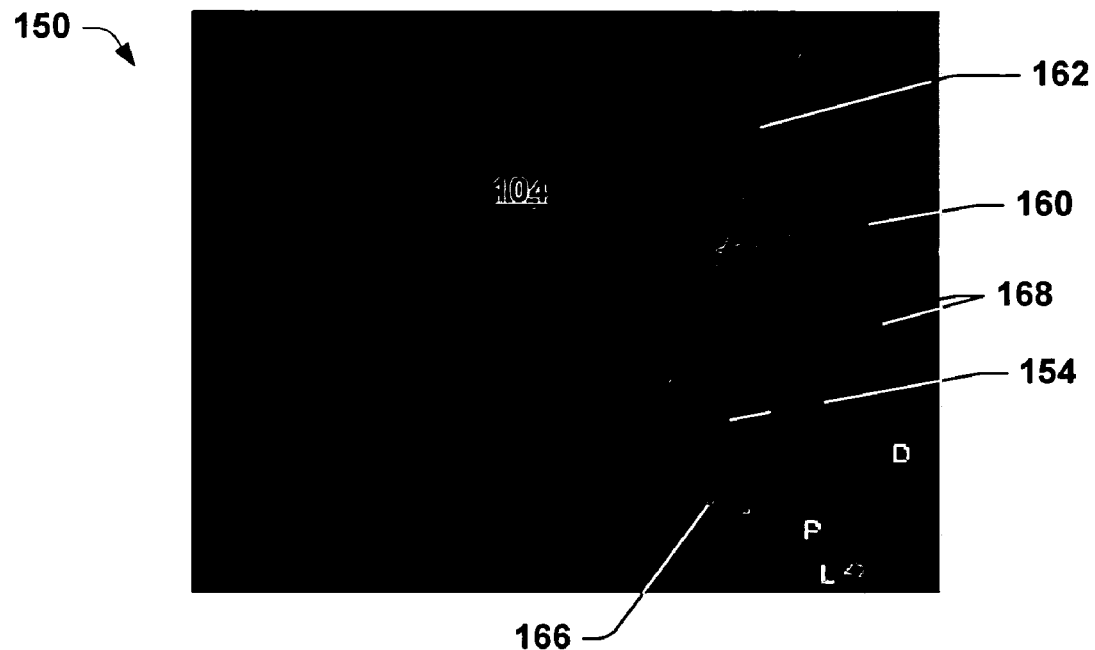
FIG. 7 depicts an example of a volume of tissue activation that can be ascertained for an isotropic tissue medium.
Figure 8:
FIG. 8 depicts an example of a volume of tissue activation that can be ascertained for an anisotropic and inhomogeneous tissue medium.

By way of further example, FIGS. 7 and 8 depict example images 150 and 152, respectively, demonstrating different VTAs that can be determined for deep brain stimulation by applying different tissue models for the same activating function. For sake of consistency, similar reference characters refer to the same structural and anatomical parts in each of the FIGS. 7 and 8.

In FIG. 7, the VTA, indicated at 154, is determined for a tissue model where the tissue medium is represented as being isotropic and homogeneous. In FIG. 8, the image 152 demonstrates the VTA, indicated at 156 for a model that represents the tissue medium as being inhomogeneous and anisotropic (a more complex and usually more accurate tissue representation), such as a DTI-based tissue medium. A comparison of the approaches demonstrates the resulting differential activation of surrounding anatomical structures.

Each of the tissue models utilized to derive the images of FIGS. 7 and 8 includes a tissue encapsulation layer 160 around the electrode shaft 162. The electrode shaft 162 extends through the thalamus 164 and terminates with its distal end located within or adjacent the subthalamic nucleus (STN) 166. A plurality of electrode contacts 168 are disposed in a spaced apart relationship along the length of the shaft 162. The VTA 154 corresponds to a volume of tissue within a boundary defined by activating function applied for a given set of stimulation parameters one of the contacts 168 within the STN 166. In FIG. 8, the VTA 156 similarly corresponds to a volume of tissue within a boundary defined by activating function applied for the same given set of stimulation parameters at a single contact within the STN 166. The VTA 154 (FIG. 7) and the VTA 156 (FIG. 8) generated under the two conditions were matched for electrode impedance.

Referring back to FIG. 4, the system 100 also includes a VTA evaluation block 120 that is operative to search through the VTAs to determine the target VTA 104 for achieving a desired therapeutic effect. The evaluation block 120 can be implemented as a computer-implemented (or computer-assisted) algorithm that evaluates the candidate VTAs 102 in the search space. The evaluation block, for example, can include a scoring function 122 that assigns a score to each candidate 120 VTA. The score can help a user select the target VTA from the VTA search space. Alternatively, the evaluation block 120 can automatically select the target VTA based, at least in part, on the score provided for each VTA 102 in the search space. The VTAs and their scores can be displayed to a user, such as by providing corresponding data to a display or other output device (e.g., a printer).

As one example, the evaluation algorithm of the evaluation block 120 can employ one or more criteria that establishes: (a) one or more regions in which activation is desired; or (b) one or more regions in which activation should be avoided. For example, the scoring function 122 can determine a score of how each candidate VTA maps against desired and undesired regions. In one example, the scoring function computes the score as a function of the number of VTA voxels that map to the one or more regions in which activation is desired, and the number of VTA voxels map to the one or more regions in which activation is undesired. As another example, these two quantities may be weighted differently such as, for instance, if avoiding activation of certain regions is more important than obtaining activation of other regions (or vice-versa). In yet another example, these two quantities may be used as separate scores. As another example, the evaluation block 120 and scoring function 122 can be implemented based on documented therapeutic effect and assign a corresponding raw score to each VTA and its associated stimulation parameters.

By way of further example, for the example of employing the system 100 to determine a target VTA for treatment of Parkinson's disease, the raw score provided by the scoring function 122 can correspond to documented improvement according to blinded Unified Parkinson's Disease Rating Scale (UTPDRS) evaluation. The VTAs can also be designated with one or more primary symptoms of improvement, such as rigidity, bradykinesia, and/or tremor. The VTA can also be designated as being non-therapeutic when a given VTA is identified with a clinically defined side effect type (e.g., muscle contraction, parasthesia, and the like). The designation symptomatic relief and side effects can also be weighted and applied to scoring criteria according to the perceived conditions (e.g., through clinical testing) associated with a given VTA. Other scoring criteria can exist for Parkinson's disease as well as for other types of disorders that can be utilized by the evaluation block 120. The scoring function 122 thus can provide an indication of the therapeutic and non-therapeutic effect associated with the VTAs 102.

A 3D probabilistic map or functional VTA atlas can also be generated from the VTA data 102, which that can further be utilized to determine the target VTA 104. The VTA data, for example, can be acquired for plurality (e.g., hundreds or thousands) of patients so that VTA 102 for each patient can provide quantitative relationship between the VTA and a desired therapeutic effect for the patients. For example, each of the VTAs 102 can be broken up into a voxelized grid in which each voxel retains the score determined for the respective VTA. The voxel matrix can be statistically analyzed to provide a corresponding probability value for each voxel in the matrix that represents a statistical score for each voxel in the functional atlas. With a sufficiently large search space, a corresponding target VTA thus can be identified based on the aggregate set of VTAs 102 in the search space. Side effect pathways can also be integrated into the 3D probabilistic map of therapeutic VTAs as areas to avoid when defining the target VTA 104. The resulting probabilistic VTA map can be utilized to determine the target VTA based on imaging data for a given patient. Those skilled in the art will understand various other approaches that can be employed to determine the target VTA from a given search space of VTAs based on the teachings contained herein. For example, the target VTA can also be user defined, such as based on clinical testing or empirical testing or a combination of clinical and empirical testing.

Figure 9:
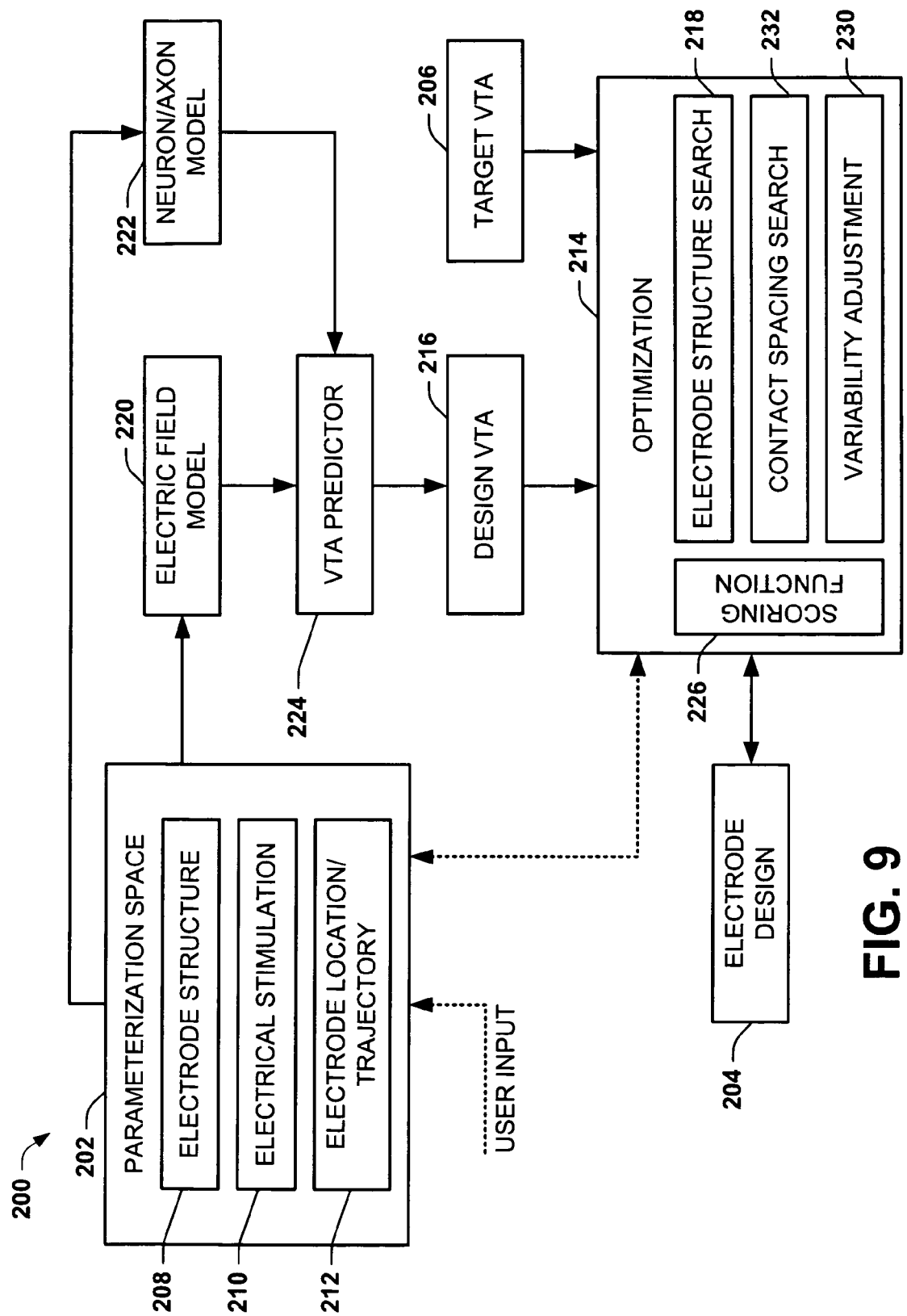
FIG. 9 depicts an example of a design system that can be implemented according to an aspect of the invention.

FIG. 9 depicts an example of an electrode design system 200 that can be implemented according to an aspect of the invention. The system 200 can be implemented as computer-executable instructions running in one or more computers or other processor-based systems. The system 200 includes a parameterization space 202 that includes parameters that represent one or more design parameters that can be varied to provide an electrode design 204 for achieving a desired therapeutic effect. The purpose of the system 200 is to determine which parameter or combination of plural design parameters can best match a target volume of tissue activation (VTA) 206. One or more of the parameters for the electrode design or available ranges can be established by a user input, for example.

The target VTA 206 defines a region of tissue that, if stimulated by an electric field from the electrode located therein, generates an action potential that has been determined to achieve a desired therapeutic effect. The therapeutic effect and the location of the target VTA 206 can vary according to the disorder of a particular patient. The target VTA 206 can be predetermined for a given patient, such as based on simulation, clinical testing or a combination of simulation and clinical testing (e.g., see FIG. 4 and the corresponding description). Alternatively, the target VTA 206 can be computed by the system 200 in conjunction with the determination of the electrode design 204. The VTA for a given electrode design varies as a function of geometry (e.g., height, diameter, and spacing) of the individual cylindrical electrode contacts of the electrode.

Figure 10:
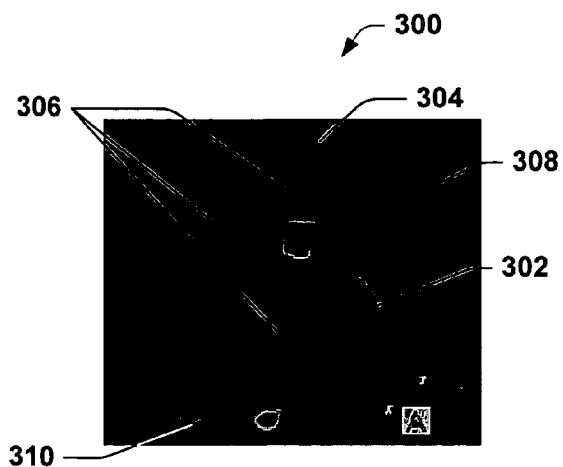
FIG. 10 depicts an example image of a target VTA that can be used for designing an electrode according to an aspect of the invention.

As an example, FIG. 10 depicts an image 300 that includes a representation of a target VTA 302 that can be utilized to determine the electrode design for a given target nucleus. As shown in FIG. 10, an electrode 304 includes a plurality of contacts 306, at least one of which is located in the target VTA 302. The electrode shaft extends through the thalamus 308 and through at least a portion of the STN 310. In the example of FIG. 10, the target VTA 302 encompasses the dorsal STN and ZI/H2, such as represents a preliminary definition of a target VTA for STN DBS. Those skilled in the art will appreciate that the design system 200 (FIG. 9) is applicable to determining target VTAs for other nuclei in the brain as well as in other anatomical regions.

Referring back to FIG. 9, the parameterization space 202 includes a range of electrode structure parameters 208. For the example of an electrode having a plurality of cylindrical electrode contacts, the electrode structure parameters 208 can include the height, diameter and spacing (or distribution) of the electrode contacts along the electrode shaft. As an example, a predefined range of values for the height and diameter parameters can be stored as part of the parameterization space (e.g., by setting limits for minimum and maximum height and diameters). Relationships between parameters can also be parameterized, such as the aspect ratio (d/h). The aspect ratio further can be utilized to constrain the optimization procedure, such as by limiting the search space to a predefined range of aspect ratios (e.g., d/h<some predefined value), which can be set according to the shape and size of the target VTA 206.

The parameterization space 202 can also include electrode stimulation parameters 210, such as voltage or current amplitude, frequency, pulse width and pulse shape. The stimulation parameters can be applied to one or more electrode contacts uniformly or different set stimulation parameters can be applied to each electrode contact independently of the other electrode contacts. The contact location and trajectory of the electrode within an anatomical region can be included as parameters 212 in the parameterization space 202 identifying relative electrode and contact placement in an anatomical region. For example, the contact location can be centered in the anatomical region defined by the target VTA 206 and the trajectory can be set to a corresponding standard trajectory for the target nucleus. Alternatively, such parameters can be varied, as described with respect to other example embodiments described herein.

An optimization method 214 controls the parameter searching over the parameterization space 202. The optimization method 214 can evaluate a design VTA 216 for an instance of the parameterization space 202 relative to the target VTA 206 to ascertain which instance (or subset of instances) of the parameterization space provides a design VTA that best matches the target VTA. The optimization method 214 can include one or more search algorithms programmed to determine the electrode design 204.

As one example, the optimization method 214 can include an electrode structure search 218 that is programmed to search the parameterization space 202 to determine one or more instances of electrode structure parameters. For example, the electrode structure search 218 can initialize the parameterization space 202 to set the electrode structure parameters 208 (height and diameter) to predetermined dimensions, such as can be arbitrarily set or can be set based on various criteria (e.g., empirical or clinical studies). The electrode location/trajectory parameters 212 can remain fixed during application of the electrode structure search 218. The electrical stimulation parameters 210 can be varied for a given set of electrode structure parameters 208 to provide maximal design VTA coverage relative to the target VTA 206, as described herein.

The system 200 includes an electrode field model 220 and a tissue model 222 that are employed by a VTA predictor 224 to determine the design VTA 216 for a given instance or over a set of plural instances of the parameterization space 202. The VTA predictor 224 predicts the neural response to stimulation, corresponding to the design VTA 216, by applying the potential distribution of the electrical field model 220 to the neuron/axon model 222. The neural response to extracellular stimulation is dependent on several factors, such as, for example: (1) the electrode geometry (e.g., the electrode structure parameters 208); (2) the electrode stimulation parameters 210 (e.g., stimulus waveform, stimulation frequency, pulse width, etc.); (3) the shape of the electric field (e.g., as determined by the inhomogeneous and anisotropic bulk tissue properties); (4) the neuron geometry; (5) the neuron position relative to the stimulating electrode; and ($\sigma$) the neuron membrane dynamics. Some or all these factors can be represented in the electric field model 220 and the neuron/axon model 222.

As one example, the electric field model 220 can be implemented as a computer-solvable FEM mesh based on the electrode structure parameters 208 and the stimulation parameters 210 in the parameterization space 202. The electric field model 220 thus can include a stimulating electrode model that represents the morphology (or structure) of the electrode, as established by the electrode structure parameters 208 employed by the electrode structure search 218. The electric field model 220 can also include a representation of the conductivity of a thin layer of tissue encapsulating the particular electrode, which provides the electrode tissue interface. The electric field model 220 can also explicitly represent the electrode impedance and the electrode capacitance. The electric field model 220 also includes tissue conductivity model that represents the anatomical structure surrounding the electrode. As described herein, the tissue conductivity model can include data that represents inhomogeneous or anisotropic properties of the tissue near the stimulation electrode, such as can be obtained by DTI imaging or by using other techniques described herein. Alternatively, the tissue conductivity model might include data that represents tissue near the stimulation electrode as being homogeneous and isotropic, such as described herein. The electric field model 220 thus represents a potential distribution in the tissue medium for a given set of parameters (e.g., electrode structure and electrode stimulation parameters) in parameterization space 202.

The neuron/axon model 222 can include a multi-compartment neuron or axon model that positions the modeled neurons or axons at specifiable positions along one or more nerve pathways in the FEM mesh defined by the electric field model 220. In addition to properties of individual neurons, the neuron/axon model 222 may depend on one or more of the parameters (e.g., electrode structure parameters 208 and electrical stimulation parameters 210) of the stimulation being modeled. For example, the stimulation pulse width will affect the neuron response. Therefore, in one example, the neuron/axon model 222 can be tailored to a specific value for one or more DBS stimulation parameters. By way of further example, the nerve pathways can be ascertained using DTI-derived imaging data, or by using anatomic atlas data, or any other appropriate technique.

Those skilled in the art will understand appreciate various neuron models or axon modeling techniques that could be employed in the system 200. An example of an axon model is described in Cameron C. McIntyre et al., "Modeling the Excitability of Mammalian Nerve Fibers: Influence of Afterpotentials on the Recovery Cycle," J. Neurophysiology, Vol. 87, February 2002, pp. 995-1006, which is incorporated by reference herein in its entirety, including its disclosure of axon models. In another example, a more generalized neuronal model can be used, an example of which is described in Cameron C. McIntyre et al., "Cellular Effects of Deep Brain Stimulation: Model-Based Analysis of Activation and Inhibition," J. Neurophysiology, Vol. 91, April 2004, pp. 1457-1469, which is incorporated by reference herein in its entirety.

The neuron/axon model 222 describes how the neurons will respond to an applied electric field; namely whether the neuron will fire and whether the neurons will generate a propagating action potential.

As a further example, the neuron model 222 geometries are typically broken up into many (e.g., hundreds) of compartments. The VTA predictor 224 can co-register the various compartments of the neuron/axon model 222 within the FEM mesh of the electric field model 220. This co-registration allows calculation of the extracellular potentials from the applied electric field along the complex neural geometry. After the extracellular potentials are determined for each neural compartment as a function of time during the applied stimulation, for each neural position relative to the electrode, the neuron/axon model 222 can be used to test whether the applied stimulus exceeded the neural threshold that triggers an action potential.

As another example, using the neuron/axon model 222 to simulate how the neurons (located as determined from the DTI-derived conductivity data, in one example) behave, the threshold value of the second difference of electric field that will result in such propagating action potentials can be calculated. The stimulating influence of the electric field (as represented by the electric field model 220) is applied to the neuron/axon model neurons to define a threshold value. This threshold value can then used to define the boundary of the design VTA in the non-uniform conductivity tissue, similar to as discussed above with respect to FIG. 4.

The electrode structure search 218 can vary the electrode height and diameter over the range of predefined values, such as mentioned above. Corresponding design VTAs can be determined over the range of parameter values. Those skilled in the art will appreciate that various constraints that can be programmed into the electrode structure search 218 or into the parameterization space 202 to reduce computational complexity of the design system. For example, it may be desirable to constrain the diameter to height (aspect) ratio to remain below a predetermined value (e.g., d/h>1), which value further can vary according to the shape and volume of the target VTA 206. Those skilled in the art will appreciate various ways to quantify the shape and size of the target VTA 206 such that an appropriate VTA aspect ratio can be established to constrain the optimization accordingly.

The optimization method 214 can also include one or more scoring functions 226 that are employed to evaluate at least some of the design VTAs 216 in the search space relative to the target VTA 206. Different search components of the optimization method can utilize the same scoring function or different scoring functions can be utilized for different searches. As one example, each design VTA (corresponding to an iteration of the electrode structure search 218) can be scored according to the following equation:

$$\text{Score} = (\text{VTA}_{in\ target}/\text{VTA}_{target}) * (-\text{VTA}_{out\ target}/X\text{volume}),\quad \text{Equation 3}$$

where:
VTA$_{in\ target}$ corresponds to the portion of the design VTA 216 that resides within the target VTA 206,
VTA$_{out\ target}$ corresponds to the portion of the design VTA 216 that resides outside of the target VTA 206, and
Xvolume defines the penalty for stimulation spread outside of the target VTA.

The highest scoring electrode design VTA will represent the maximal volume overlap between the stimulation VTA and the target VTA while providing a penalty for VTA spread outside of the target VTA. In practice, variants of the above scoring equation (as well as other scoring functions) can be used to hone in on an appropriate value for the X volume parameter.

As part of the electrode structure search 218, one or more of the electrode stimulation parameters 210 can be adjusted for the given electrode structure design so that the design VTA spreads to or near to the edge of the target VTA 206. Alternatively, the electrode structure search 218 can iteratively adjust one or more electrode structure parameters while the electrode stimulation parameters remain constant, generating a new design VTA 216 for each iteration. Those skilled in the art will appreciate various approaches that can be utilized to generate design VTAs 216 over the entire or a subset of the parameterization space.

The results of the electrode structure search 218 can provide one or more electrode designs 204. For example, the electrode structure search 218 can provide a plurality of electrode designs (e.g., having defined electrode structure and electrode stimulation parameters) that result in respective design VTAs that best match the target VTA 206.

Figure 11:
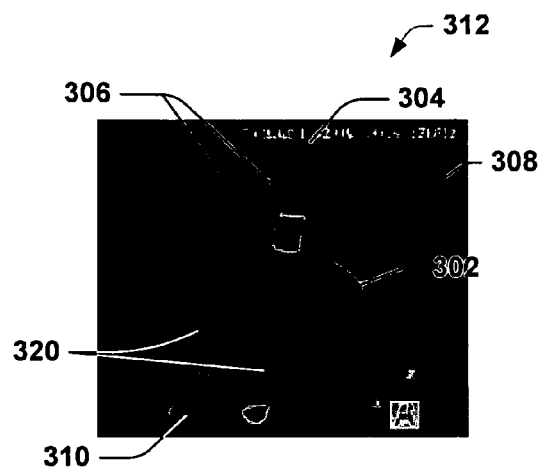
FIG. 11 depicts an example of a first design VTA overlayed on the image of FIG. 10.
Figure 12:
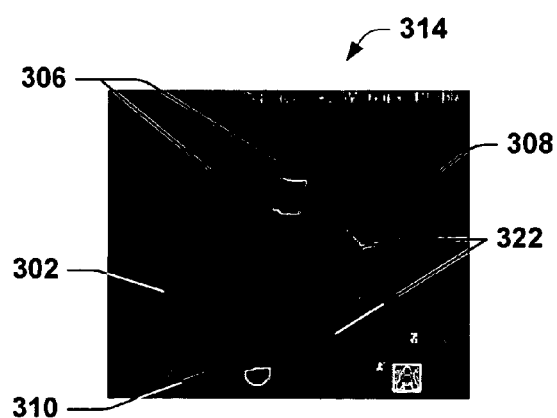
FIG. 12 depicts an example of a second design VTA overlayed on the image of FIG. 10.
Figure 13:
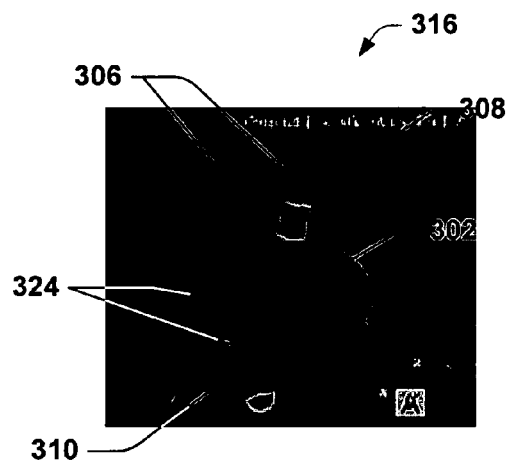
FIG. 13 depicts an example of a third design VTA overlayed on the image of FIG. 10.
Figure 14:
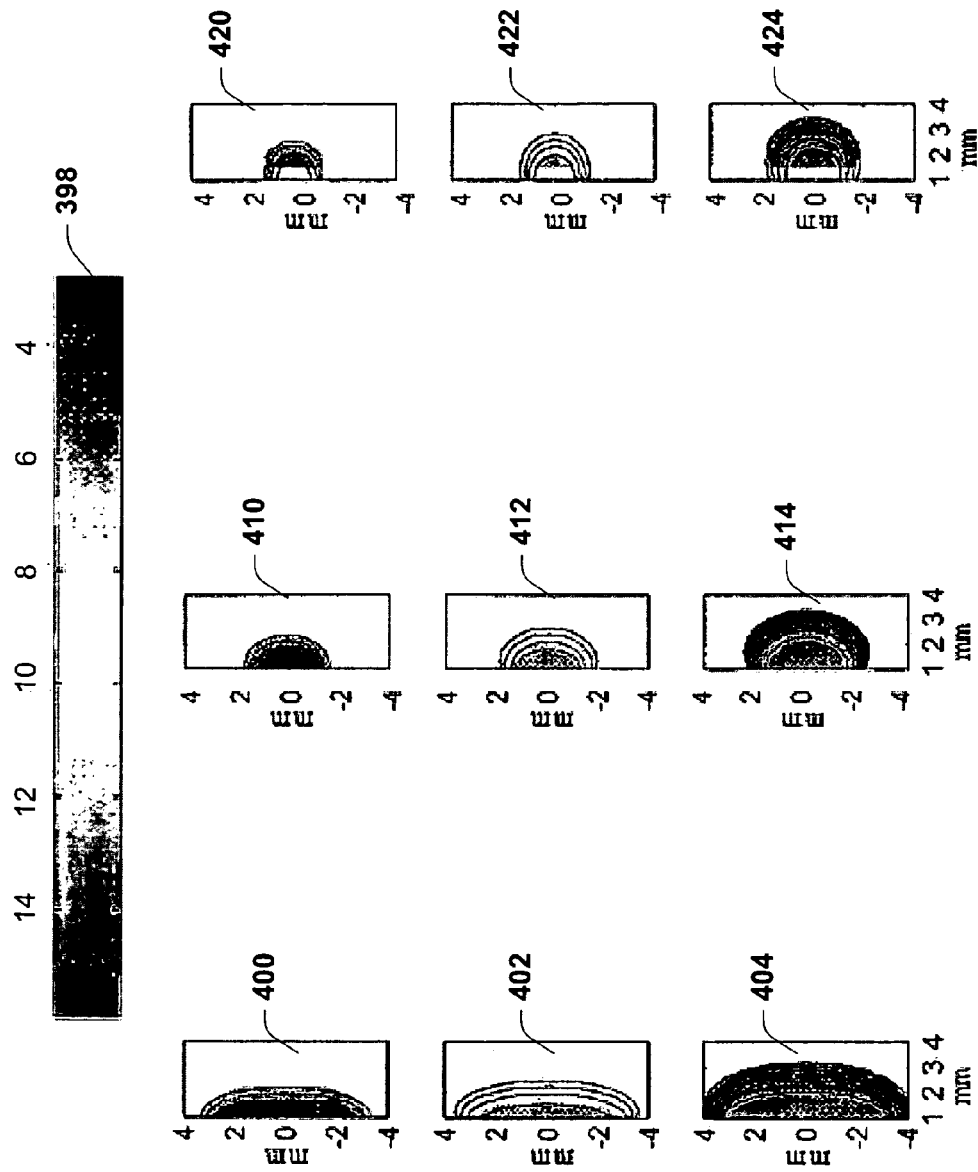
FIG. 14A depicts examples of contour plots for second difference threshold values for a first electrode design at different stimulation parameters that can be used for designing an electrode according to an aspect of the invention.
FIG. 14B depicts examples of contour plots for second difference threshold values for a second electrode design at different stimulation parameters that can be used for designing an electrode according to an aspect of the invention.
FIG. 14C depicts examples of contour plots for second difference threshold values for a third electrode design at different stimulation parameters that can be used for designing an electrode according to an aspect of the invention.

By way of illustration, FIGS. 11, 12 and 13 depict images 312, 314 and 316, respectively, that include example design VTAs generated for electrode contact 1 of a given electrode structure (e.g., as defined by electrode structure parameters 208) 304 for different stimulation parameters. In FIGS. 11, 12 and 13, the same reference numbers are used to refer to the same structural parts as introduced with respect to FIG. 10. The VTAs generated at contact 1 result in some amount of $VTA_{in\ target}$ and some amount of $VTA_{out\ target}$, both of which vary as a function of the stimulation parameter settings and the electrode contact geometry. In FIG. 11 the image 312 includes a design VTA 320 for a stimulation voltage at contact 1 of about −2 V. In FIG. 12, the image 314 includes a design VTA 322 for a stimulation voltage at contact 1 of about −2.5 V. In FIG. 13, the image 316 includes a design VTA 324 for a stimulation voltage at contact 1 of about −3 V. In FIGS. 10, 11, 12 and 13, for purposes of simplicity of explanation and for sake of comparison, it is assumed that the electrode geometry remains constant. By applying the above scoring criteria, the example of FIG. 12 has the highest score and, thus, can be utilized to establish the electrical stimulation parameters 210 associated with the given set of electrode structure parameters 208 for the electrode design of FIG. 9. It will be appreciated that more than three different stimulation parameters can be evaluated and scored as part of the electrode structure search 218.

Referring back to FIG. 9, it is again noted that the electrode location/trajectory parameters 212 can remain fixed during the optimization of electrode design associated with the electrode structure search 218 and a contact spacing search 232 (when implemented). The surgical trajectory for electrode implantation in a given nucleus is relatively standardized. As one example, a general trajectory for STN DBS approximately 65 degrees up from the axial plane and approximately 10 degrees off the saggital plane. As another example, the general trajectory for GPi DBS can be approximately 70 degrees up from the axial plane and approximately 5 degrees off the saggital plane. The particular trajectory used in an individual patient, however, is chosen based on pre-operative imaging data to avoid major blood vessels, sulci, and the ventricles.

The electrode/location and trajectory parameters 212 thus can be set to standard electrode trajectories for a given nucleus (adjusted to avoid major blood vessels, sulci, and the ventricles) with the contact location at the anatomical center of the nucleus. The parameter values can remain fixed during the electrode structure search 218, such as described above.

After a subset of one or more electrode designs has been determined for the target VTA, the optimization method 214 can vary electrode structure and stimulation parameters to accommodate surgical variability (e.g., associated with surgical placement of the electrode) and anatomical variability (e.g., associated with imaging techniques for determining anatomical and electrical models).

The optimization method 214 can also include a variability adjustment component 230. The adjustment component 230 can refine a portion of the search space to and reevaluate the efficacy of one or more electrode designs to account for variability that would be expected clinically. One source of clinical variability is the stereotactic accuracy of the electrode placement. For example, it has been determined that there exists approximately 1 mm of uncertainty in all directions in three dimensional space when implanting many types of electrodes, such as DBS electrodes. Therefore, the variability adjustment component 230 can reevaluate the electrode structure parameters for each of a plurality of best-performing electrode contact designs 204, such as by adjusting the electrode location/trajectory parameter 212 to reflect the uncertainty in three-dimensional space.

As an example, a plurality (e.g., two or more, such as five) of the top scoring electrode contact designs 204 for the target VTA 206 can be subjected to further analysis. For example, the electrode location and trajectory can be incrementally adjusted (e.g., relative to the geometric center of the target VTA) in the dorsal/ventral, anterior/posterior, and medial/lateral directions) and the resulting design VTAs 216 can be scored according the sub-optimal electrode placements. The electrodes location parameters can be adjusted, for example, in predetermined increments that are less than or equal to the amount of defined variation.

The surgical trajectory of the electrode in the 3D anatomical region can also be varied, such as in a plurality of increments over a range (e.g., +/−5 degrees) relative to the axial plane and in similar increments over a range (e.g., +/−5 degrees) relative to the saggital plane. Each of the finalist DBS electrode contact designs 204 will thus be assigned a plurality of scores for each associated design VTAs 216 resulting from the incremental adjustments (to accommodate variation in location and trajectory). The set of VTA scores for each respective electrode design 204 being reevaluated can be aggregated to provide an aggregate total score for each design. The average VTA scores for each electrode design 204 further can be averaged and the highest scoring electrode design can be selected as representing an optimal DBS electrode contact for the given target nucleus. The same scoring function 226 can be utilized by the variability adjustment component 230 as is used by the electrode structure search 218. Alternatively, different scoring functions could be utilized, such as by applying weighting differently according to variations in the electrode/trajectory parameters 212 differently (e.g., imposing an increased penalty as the variations increase).

By way of example, existing neurostimulation devices are being equipped with current steering capabilities (e.g., implantable pulse generators having 8 or 16 independent current sources). The existence of current steering technology in neurostimulation becomes an attractive mode of operation in a situation where two (or more) contacts are located within the target VTA, but neither is in a position to adequately stimulate the target VTA without spreading stimulation into neighboring side effect regions. A possible solution would be to balance stimulation through the two contacts, possibly with unequal stimulus amplitudes, such that the target VTA is maximally stimulated.

The optimization method 214 can also employ a contact spacing search 232 to define a contact spacing that further maximizes the design VTA coverage with respect to the target VTA 206. Based on current steering analysis, there exists a contact spacing that maximizes VTA coverage along the trajectory of the electrode shaft. The optimization method 214 can employ the contact spacing search 232, such as in situations when more than one electrode contact will be activated to supply electric fields that may interact spatially and/or temporally. As one example, the optimization method 214 can activate the contact spacing search 232 to evaluate the effects of current-steering, such as in situations when the top scoring electrode design fails to meet a minimum score relative to the target VTA 206.

As one example, the contact spacing search 232 can search the parameterization space 202 according to spatially and/or temporally overlapping electric fields generated from multiple electrodes. The contact spacing search 232 can score the resulting design VTAs to determine which design or set of electrode designs having multiple contacts with independently controllable sources, best matches the target VTA. It should be noted that the electrode structure search 218 can be implemented as part 8 of the contact spacing search 232. As a result, the combination of electrode structure search 218 and the contact spacing search 232 can be employed to identify a contact spacing in conjunction with other electrode structure parameters (e.g., height and diameter for each contact) 208 that, height and diameter, will afford a maximal VTA coverage along the trajectory of the electrode shaft.

Thus, the contact spacing search 232 can be utilized to adjust the spacing between one or more pairs of electrodes in the electrode design 204 to determine spacing parameters for the electrode design that provides a design VTA 216 that more closely matches the target VTA 206.

The impact of electrode trajectory variability and electrode location variability can be evaluated with respect to the added VTA coverage that can be attained with current steering contacts. The contact spacing search 232 can result in the electric field model 220 representing two or more electric field distributions, which can overlap according to the spacing and charge distribution of the respective fields. The spacing between electrode contacts can be defined in the parameterization space 202 by appropriate spacing parameters in the electrode structure parameters 208. Those skilled in the art will understand ways to construct appropriate electric field model 220 for the multiple contact electrode based on the teachings contained herein.

The variability adjustment 230 can also be utilized in conjunction with the contact spacing search 232 and the resulting multi-contact electrode design 204, similar to as described with respect to the single contact methodology. The variability adjustment component can thus identify a theoretically optimal trajectory that should be used with the determined optimal contact design and contact spacing (e.g., as defined by the electrode structure parameters 208 of the resulting electrode design 204).

In view of the foregoing, it will be appreciated that the design system 200 thus can provide a nuclei-specific single contact electrode design or a multiple contact design that is customized to the anatomical and electrical constraints of the target nucleus (e.g., the STN or GPi). By also accounting for the potential variability in electrode placement and trajectory, such an electrode design should afford increase resilience to surgical placement variability while also maximizing VTA coverage of the target VTA. As described herein, the resulting stimulation parameters for the electrode design can be employed to program an LPG or other stimulation device for applying stimulation to an electrode constructed according to the structural parameters, thereby achieving neurostimulation that substantially matches the target VTA.

By way of further illustration, FIGS. 14A, 14B and 14C depict the effects of different electrode contact geometries on the design VTA. The example FIGS. 14A, 14B and 14C illustrate the VTA as contour plots for second difference threshold values (similar to FIG. 6). The scale that defines the second difference threshold is indicated above the figures (indicated at 398). Each contour plot depicts the VTA at four voltage values (e.g., −0.4 V, −0.6 V, −0.8 V, −1.0 V) for stimulation at 130 Hz. The plots in the respective figures also have be generated for a constant surface area electrode contact geometry; although, as described herein, the surface area of an electrode contacts need not (and typically will not) remain constant when determining an electrode design for a target VTA according to an aspect of the invention.

Figure 15:
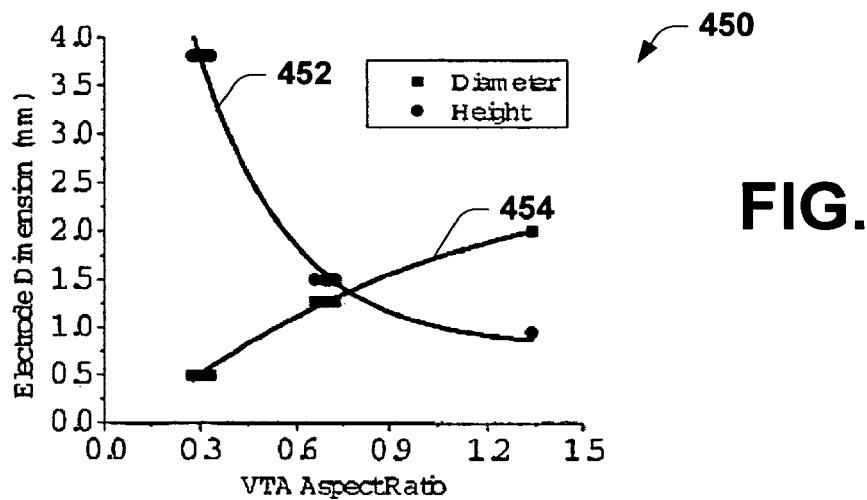
FIG. 15 depicts a graph of electrode dimensions plotted as a function of VTA aspect ratios for example design parameters.
Figure 16:
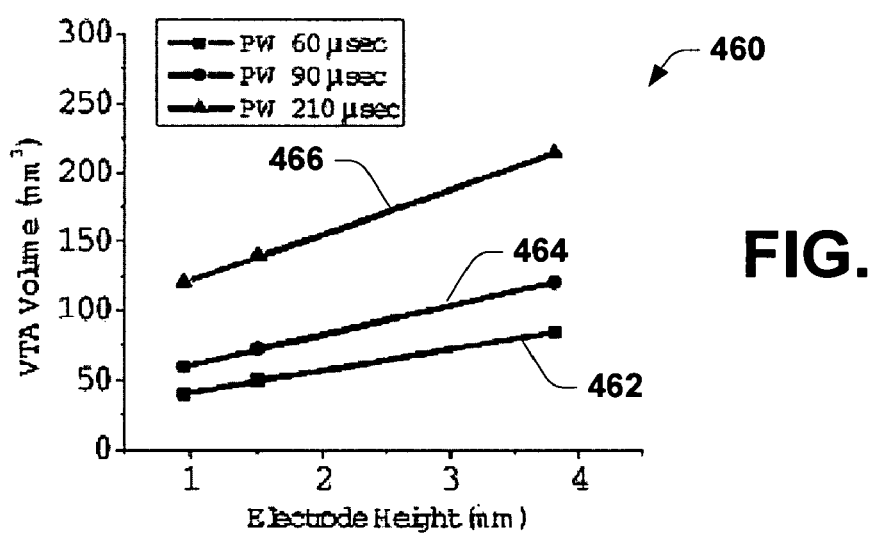
FIG. 16 depicts a graph of VTA volume plotted as a function of electrode height for example design parameters.
Figure 17:
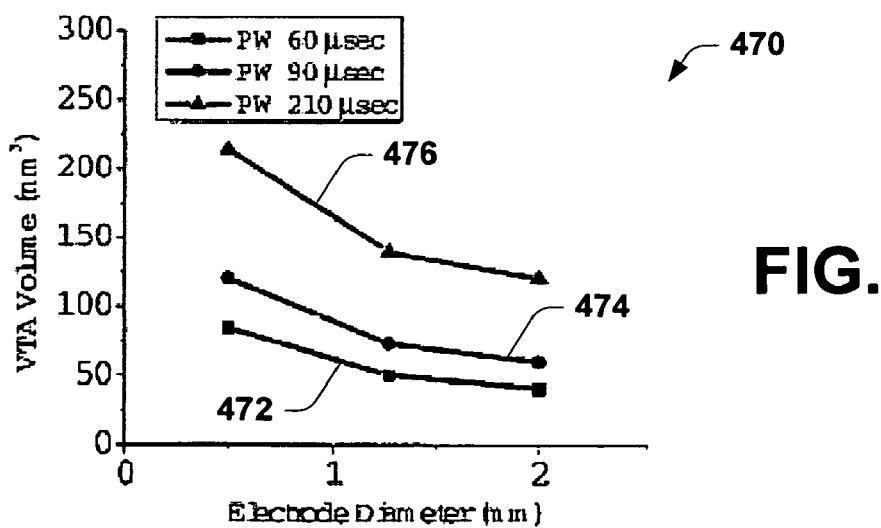
FIG. 17 depicts a graph of VTA volume plotted as a function of electrode diameter for example design parameters.

FIG. 14A demonstrates contour plots 400, 402 and 404 for second difference threshold values for an electrode contact geometry (e.g., that can be characterized as tall and skinny) having a diameter of 0.5 mm and a height of 3.81 mm. The plots 400, 402 and 404 each have a different pulse width, such as about 60 μsec, 90 μsec, and 210 μsec. FIG. 14B demonstrates contour plots 410, 412 and 414 for second difference threshold values for an electrode contact geometry having a diameter of 1.27 mm and a height of 1.5 mm. The plots 410, 412 and 414 each have a different pulse width, such as about 60 μsec, 90 μsec, and 210 μs (the same as in the other figures for sake of comparison). FIG. 14C demonstrates contour plots 420, 422 and 424 for second difference threshold values for an electrode contact geometry (e.g., that can be characterized as short and fat) having a diameter of 2.0 mm and a height of 0.475 mm. The plots 400, 402 and 404 each have a different pulse width, such as about 60 μsec, 90 μsec, and 210 μsec. Thus, the examples in FIGS. 14A, 14B and 14C demonstrate that the VTA aspect ratio To further demonstrate the effects of electrode contact geometry, can provide a useful metric to quantity VTA shape and size. FIGS. 15 16 and 17 illustrate different measures and relationships that characterize VTA shape and volume relative to electrode geometry based on the results shown in FIGS. 14A, 14B and 14C. The information portrayed in the FIGS. 15, 16 and 17 demonstrates that VTA shape and volume can be modulated by simply changing the electrode geometry. For example, FIG. 15 depicts a graph 450 that plots electrode dimensions (height and diameter) as a function of VTA aspect ratio. The VTA aspect ratio is determined by dividing the VTA by the height for plot 452 and by the diameter for plot 454. The graph 450 thus includes a plot 452 of height as a function of VTA aspect ratio and a plot 454 of diameter as a function of the VTA aspect ratio.

FIG. 16 depicts a graph 460 of VTA volume plotted as a function of electrode height for each of the pulse widths from FIGS. 14A, 14B and 14C, which plots are indicated at 462, 464 and 466. The plot 462 represents the VTA volume as function of height for the 60 μsec, plot 464 corresponds to the 90 μs pulse width, and plot 466 corresponds to the 210 μs pulse width. From FIG. 16, it can be demonstrated that, for a given set of electrode geometry, increases in electrode height cause a substantially linear increase in VTA volume, and that the rate of increase is dependent on the pulse width.

FIG. 17 depicts a graph 470 of VTA volume plotted as a function of electrode diameter for each of the pulse widths from FIGS. 14A, 14B and 14C, which plots are indicated at 472, 474 and 476. From the plots 472, 474 and 476, it can be shown that increases in electrode contact diameter cause a nonlinear (e.g., nonlinear) logarithmic decrease in VTA volume, which amount of decrease is dependent on stimulation pulse width.

In view of the foregoing, it will be appreciated that additional variations in the VTA shape can be achieved by adjusting other design parameters, such as the number of contacts and spacing, the electrical stimulation parameters and the like. Those skilled in the art will appreciate that the methods and systems described herein can be employed to customize an electrode design to maximize VTA spread for a given target nucleus.

Figure 20:
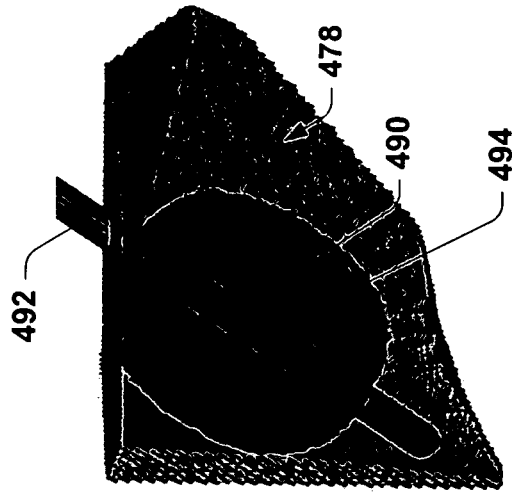
FIG. 20 depicts an image representing an example design VTA superimposed on the target VTA of FIG. 18 for a second electrode design.
Figure 19:
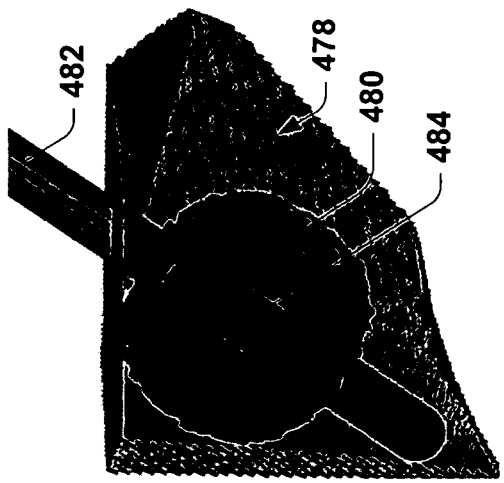
FIG. 19 depicts an image representing an example design VTA superimposed on the target VTA of FIG. 18 for a first electrode design.
Figure 18:
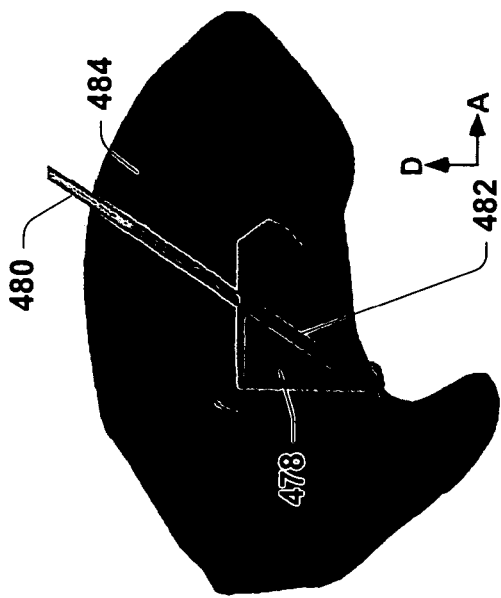
FIG. 18 depicts an image representing an example target VTA in the thalamus.

By way of further example, FIGS. 18, 19 and 20 demonstrate the effects of electrode geometry on VTA for a particular nucleus, namely the ventral intermediate nucleus of the thalamus (VIM) 478. In particular, FIG. 18 depicts an electrode 480 having a single contact 482 inserted into the thalamus 484. In the example of FIG. 18 the electrode is positioned at the anatomical center of the VIM 478. The VIM is a long narrow nucleus measuring approximately 8 mm (dorsal-ventral) by approximately 3 mm (anterior-posterior) by approximately 12 mm (medial-lateral).

FIG. 19 depicts a VTA 480 for an electrode 482 having first electrode design parameters. In the example of FIG. 19, the electrode 482 includes a contact 484 that corresponds to a standard electrode contact geometry (e.g., having a height of approximately 1.5 mm, diameter of approximately 1.27 mm, providing a surface area≈6 mm$^2$), with stimulation settings of −1 V and 90 μs pulse width at 130 Hz. The aspect ratio (d/h) of the electrode contact 484 is approximately 0.4. The electrode design of FIG. 19 produces the VTA 480 to fills approximately 26% of the VIM 478 before spreading outside the target VTA defined by the VIM.

FIG. 20 depicts a VTA 490 for an electrode 492 having a second (customized) electrode design parameters, which are different from those of the electrode 482 of FIG. 19, such as may be determined according to an aspect of the invention. In the example of FIG. 20, the electrode includes a contact 494 that is also positioned at the anatomical center of the VIM. The electrode contact 494 is designed with a diameter of approximately 0.75 mm and a height of approximately 2.54 mm height to provide an aspect ratio of approximately 0.4, which more closely matches the aspect ratio of the VIM 478 than the example electrode in the example of FIG. 19. For sake of comparison, the electrode contact 494 has approximately the same contact surface area as the example of FIG. 19 and depicts a corresponding design VTA 490 under the same stimulation (stimulation voltage of about −1 V and 90 μs pulse width). The design of FIG. 20 conditions results in better stimulation of the VIM 478 by producing a VTA that fills 33% of the volume, which is about a 28% increase compared to the VTA 480 in the example of FIG. 19. Additionally, the custom electrode design 492 can result in approximately 7% more stimulation of the VIM 478 with no increase in spread outside the boundary of the target VTA defined by the VIM.

What have been described above are examples or embodiments of the invention. It is, of course, not possible to describe every conceivable combination of components or methodologies for purposes of describing the present invention, but one of ordinary skill in the art will recognize that many further combinations and permutations of the present invention are possible. Accordingly, the invention is intended to embrace all such alterations, modifications and variations that fall within the invention claimed herein. In the claims, unless otherwise indicated, the article "a" refers to "one or more than one".

What is claimed is:

1. A method for determining an electrode design, comprising:

selecting an anatomical region to achieve a desired therapeutic effect;

defining a target volume of tissue activation in the selected anatomical region expected to achieve the desired therapeutic effect;

determining at least one electrode structure parameter and at least one stimulation parameter that provides a design volume of tissue activation that substantially matches the target volume of tissue activation;

storing the determined at least one electrode structure parameter and the at least one stimulation parameter to define the electrode design.

2. The method of claim 1, wherein the at least one electrode structure parameter comprises dimensions for at least one contact of the electrode design.

3. The method of claim 2, wherein the dimensions for the at least one contact further comprise a dimension along a longitudinal axis and a cross-sectional dimension.

4. The method of claim 1, wherein a parameter search space is provided that includes a plurality of electrode structure parameters and a plurality of stimulation parameters, the determination further comprising:

searching through the parameter search space to ascertain which combination of the plurality of electrode structure parameters and a plurality of stimulation parameters produces an electrode design expected to substantially match the target volume of tissue activation.

5. The method of claim 4 further comprising:

selecting a subset of plural electrode designs expected to substantially match the target volume of tissue activation;

characterizing changes in the design volume of tissue activation for each electrode design in the selected subset according to changes in at least one of contact location parameter and electrode trajectory parameter; and identifying which electrode design in the selected subset exhibits increased resilience, relative to other electrode designs, to the changes in at least one of contact location parameter and electrode trajectory parameter.

6. The method of claim 1 wherein the at least one structural parameter comprises an aspect ratio defined by a ratio of a diameter and a length of the contact dimensions.

7. The method of claim 1, wherein the electrode design comprises a plurality of contacts spaced apart from each other along a longitudinal axis, the at least one structural parameter further comprising a relative spacing between at least two of the plurality of contacts along the longitudinal axis.

8. The method of claim 1, further comprising generating a score for the design volume of tissue activation to characterize an amount of overlap between the design volume of tissue activation and the target volume of tissue activation.

9. The method of claim 8, wherein the scoring further comprising applying a penalty to the score according to a spread of the design volume of tissue activation that extends outside the boundary of the target volume of tissue activation.

10. The method of claim 1, wherein the determination of the design volume tissue activation further comprises predicting effects of neural stimulation, according to the at least one electrode structure parameter and at least one stimulation parameter, for the anatomical region based on at least one threshold that characterizes an activation potential for the anatomical region in response to electrical stimulation.

11. The method of claim 1, wherein the defined target volume of tissue activation comprises a probabilistic definition that represents the anatomical region expected to achieve the desired therapeutic effect.

\* \* \* \* \*